(12) United States Patent
Yang et al.

(10) Patent No.: US 7,425,292 B2
(45) Date of Patent: Sep. 16, 2008

(54) THIN FILM WITH NON-SELF-AGGREGATING UNIFORM HETEROGENEITY AND DRUG DELIVERY SYSTEMS MADE THEREFROM

(75) Inventors: Robert K. Yang, Flushing, NY (US); Richard C. Fuisz, McLean, VA (US); Gary L. Myers, Kingsport, TN (US); Joseph M. Fuisz, McLean, VA (US)

(73) Assignee: MonoSol Rx, LLC, Portage, IN (US)

( * ) Notice: Subject to any disclaimer, the term of this patent is extended or adjusted under 35 U.S.C. 154(b) by 621 days.

(21) Appl. No.: 10/074,272

(22) Filed: Feb. 14, 2002

(65) Prior Publication Data

US 2003/0107149 A1    Jun. 12, 2003

Related U.S. Application Data

(60) Provisional application No. 60/328,868, filed on Oct. 12, 2001.

(51) Int. Cl.
*B32B 43/00* (2006.01)
*B29D 7/01* (2006.01)
(52) U.S. Cl. .................... 264/172.19; 264/212; 264/217
(58) Field of Classification Search ............ 264/172.19, 264/173.1, 175, 212, 217, 211.12, 260, 234; 424/484, 488; 484/434, 435; 34/509, 502, 34/493, 443
See application file for complete search history.

(56) References Cited

U.S. PATENT DOCUMENTS

| 307,537 A | 11/1884 | Foulks |
|---|---|---|
| 688,446 A | 12/1901 | Stempel |
| 2,142,537 A | 1/1939 | Tisza |
| 2,277,038 A | 3/1942 | Curtis |
| 2,352,691 A | 7/1944 | Curtis |
| 2,501,544 A | 3/1950 | Shrontz |
| 2,980,554 A | 4/1961 | Gentile et al. |
| 3,249,109 A | 5/1966 | Maeth et al. |
| 3,444,858 A | 5/1969 | Russell |
| 3,536,809 A | 10/1970 | Applezweig |
| 3,551,556 A | 12/1970 | Kliment et al. |
| 3,598,122 A | 8/1971 | Zaffaroni |
| 3,632,740 A | 1/1972 | Robinson et al. |
| 3,640,741 A | 2/1972 | Etes |

(Continued)

FOREIGN PATENT DOCUMENTS

DE    2432925 B2    1/1976

(Continued)

OTHER PUBLICATIONS

Dr. June V. Engel, The Benefits of Eating Fibre from http://www.diabetes.ca/Section_About/fibre.asp.*

(Continued)

*Primary Examiner*—Philip C Tucker
*Assistant Examiner*—Sing P Chan
(74) *Attorney, Agent, or Firm*—Hoffmann & Baron, LLP

(57) ABSTRACT

The invention relates to the film products and methods of their preparation that demonstrate a non-self-aggregating uniform heterogeneity. Desirably the films disintegrate in water and may be formed by a controlled drying process, or other process that maintains the required uniformity of the film.

22 Claims, 2 Drawing Sheets

U.S. PATENT DOCUMENTS

| | | | |
|---|---|---|---|
| 3,641,237 A | 2/1972 | Gould et al. | |
| 3,731,683 A | 5/1973 | Zaffaroni | |
| 3,753,732 A | 8/1973 | Boroshok | |
| 3,814,095 A | 6/1974 | Lubens | |
| 3,892,905 A | 7/1975 | Albert | |
| 3,911,099 A | 10/1975 | DeFoney et al. | |
| 3,972,995 A | 8/1976 | Tsuk et al. | |
| 3,996,934 A | 12/1976 | Zaffaroni | |
| 3,998,215 A | 12/1976 | Anderson et al. | |
| 4,029,757 A | 6/1977 | Mlodozeniec et al. | |
| 4,029,758 A | 6/1977 | Mlodozeniec et al. | |
| 4,031,200 A | 6/1977 | Reif | |
| 4,123,592 A | 10/1978 | Rainer et al. | |
| 4,128,445 A | 12/1978 | Sturzenegger et al. | |
| 4,136,145 A | 1/1979 | Fuchs et al. | |
| 4,136,162 A | 1/1979 | Fuchs et al. | |
| 4,139,627 A | 2/1979 | Lane et al. | |
| 4,226,848 A | 10/1980 | Nagai et al. | |
| 4,251,400 A | 2/1981 | Columbus | |
| 4,292,299 A | 9/1981 | Suzuki et al. | |
| 4,294,820 A | 10/1981 | Keith et al. | |
| 4,302,465 A | 11/1981 | Ekenstam et al. | |
| 4,307,075 A | 12/1981 | Martin | |
| 4,325,855 A | 4/1982 | Dickmann | |
| 4,373,036 A | 2/1983 | Chang et al. | |
| 4,406,708 A | 9/1983 | Hesselgren | |
| 4,432,975 A | 2/1984 | Libby | |
| 4,438,258 A | 3/1984 | Graham | |
| 4,460,562 A | 7/1984 | Keith et al. | |
| 4,466,973 A | 8/1984 | Rennie | |
| 4,478,658 A * | 10/1984 | Wittwer | 156/69 |
| 4,503,070 A | 3/1985 | Eby | |
| 4,515,162 A | 5/1985 | Yamamoto et al. | |
| 4,517,173 A | 5/1985 | Kizawa et al. | |
| 4,529,601 A | 7/1985 | Broberg et al. | |
| 4,529,748 A | 7/1985 | Wienecke | |
| 4,562,020 A | 12/1985 | Hijiya et al. | |
| 4,569,837 A | 2/1986 | Suzuki et al. | |
| 4,593,053 A | 6/1986 | Jevne | |
| 4,608,249 A | 8/1986 | Otsuka et al. | |
| 4,615,697 A | 10/1986 | Robinson | |
| 4,623,394 A | 11/1986 | Nakamura et al. | |
| 4,631,837 A * | 12/1986 | Magoon | 34/353 |
| 4,652,060 A | 3/1987 | Miyake | |
| 4,659,714 A | 4/1987 | Watt-Smith | |
| 4,675,009 A | 6/1987 | Hymes et al. | |
| 4,695,465 A | 9/1987 | Kigasawa et al. | |
| 4,704,119 A | 11/1987 | Shaw et al. | |
| 4,713,239 A | 12/1987 | Babaian et al. | |
| 4,713,243 A | 12/1987 | Schiraldi et al. | |
| 4,722,761 A | 2/1988 | Cartmell et al. | |
| 4,740,365 A | 4/1988 | Yukimatsu et al. | |
| 4,748,022 A | 5/1988 | Busciglio | |
| 4,765,983 A | 8/1988 | Takayanagi et al. | |
| 4,772,470 A | 9/1988 | Inoue et al. | |
| 4,777,046 A | 10/1988 | Iwakura et al. | |
| 4,789,667 A | 12/1988 | Makino et al. | |
| 4,849,246 A | 7/1989 | Schmidt | |
| 4,851,394 A * | 7/1989 | Kubodera | 514/54 |
| 4,860,754 A | 8/1989 | Sharik et al. | |
| RE33,093 E | 10/1989 | Schiraldi et al. | |
| 4,876,092 A | 10/1989 | Mizobuchi et al. | |
| 4,876,970 A | 10/1989 | Bolduc | |
| 4,888,354 A | 12/1989 | Chang et al. | |
| 4,894,232 A | 1/1990 | Reul et al. | |
| 4,900,552 A | 2/1990 | Sanvordeker et al. | |
| 4,900,554 A | 2/1990 | Yanagibashi et al. | |
| 4,900,556 A | 2/1990 | Wheatley et al. | |
| 4,910,247 A | 3/1990 | Haldar et al. | |
| 4,915,950 A | 4/1990 | Miranda et al. | |
| 4,925,670 A | 5/1990 | Schmidt | |
| 4,927,634 A | 5/1990 | Sorrentino et al. | |
| 4,927,636 A | 5/1990 | Hijiya et al. | |
| 4,937,078 A | 6/1990 | Mezei et al. | |
| 4,940,587 A | 7/1990 | Jenkins et al. | |
| 4,948,580 A | 8/1990 | Browning | |
| 4,958,580 A | 9/1990 | Asaba et al. | |
| 4,978,531 A | 12/1990 | Yamazaki et al. | |
| 4,981,693 A | 1/1991 | Higashi et al. | |
| 4,981,875 A | 1/1991 | Leusner et al. | |
| 5,023,082 A | 6/1991 | Friedman et al. | |
| 5,024,701 A | 6/1991 | Desmarais | |
| 5,028,632 A | 7/1991 | Fuisz | |
| 5,044,761 A * | 9/1991 | Yuhki et al. | 366/139 |
| 5,047,244 A | 9/1991 | Sanvordeker et al. | |
| 5,064,717 A | 11/1991 | Suzuki et al. | |
| 5,089,307 A | 2/1992 | Ninomiya et al. | |
| 5,137,729 A * | 8/1992 | Kuroya et al. | 424/435 |
| 5,158,825 A | 10/1992 | Aitwirth | |
| 5,166,233 A | 11/1992 | Kuroya | |
| 5,186,938 A | 2/1993 | Sablotsky et al. | |
| 5,229,164 A | 7/1993 | Pins et al. | |
| 5,234,957 A | 8/1993 | Mantelle | |
| 5,271,940 A | 12/1993 | Cleary et al. | |
| 5,272,191 A | 12/1993 | Ibrahim et al. | |
| 5,346,701 A | 9/1994 | Heiber et al. | |
| 5,393,528 A | 2/1995 | Staab | |
| 5,411,945 A | 5/1995 | Ozaki et al. | |
| 5,413,792 A | 5/1995 | Ninomiya et al. | |
| 5,433,960 A | 7/1995 | Meyers | |
| 5,455,043 A | 10/1995 | Fischel-Ghodsian | |
| 5,462,749 A | 10/1995 | Rencher | |
| 5,472,704 A | 12/1995 | Santus et al. | |
| 5,518,902 A | 5/1996 | Ozaki et al. | |
| 5,567,431 A | 10/1996 | Vert et al. | |
| 5,620,757 A | 4/1997 | Ninomiya et al. | |
| 5,629,003 A | 5/1997 | Horstmann et al. | |
| 5,700,478 A | 12/1997 | Biegajski et al. | |
| 5,700,479 A | 12/1997 | Lundgren | |
| 5,733,575 A * | 3/1998 | Mehra et al. | 424/480 |
| 5,759,599 A * | 6/1998 | Wampler et al. | 426/89 |
| 5,766,620 A | 6/1998 | Herber et al. | |
| 5,881,476 A | 3/1999 | Strobush et al. | |
| 5,948,430 A | 9/1999 | Zerbe et al. | |
| 6,047,484 A * | 4/2000 | Bolland et al. | 34/197 |
| 6,153,210 A | 11/2000 | Roberts et al. | |
| 6,177,096 B1 | 1/2001 | Zerbe et al. | |
| 6,231,957 B1 | 5/2001 | Zerbe et al. | |
| 6,238,700 B1 * | 5/2001 | Dohner et al. | 424/484 |
| 6,284,264 B1 * | 9/2001 | Zerbe et al. | 424/435 |
| 6,428,825 B2 * | 8/2002 | Sharma et al. | 424/777 |
| 6,552,024 B1 * | 4/2003 | Chen et al. | 514/252.16 |
| 6,660,292 B2 * | 12/2003 | Zerbe et al. | 424/439 |
| 2001/0006677 A1 | 7/2001 | McGinty et al. | |
| 2001/0022964 A1 | 9/2001 | Leung et al. | |
| 2001/0046511 A1 | 11/2001 | Zerbe et al. | |

FOREIGN PATENT DOCUMENTS

| | | | |
|---|---|---|---|
| DE | 2449865 B2 | 4/1976 | |
| DE | 3630603 C2 | 3/1988 | |
| EP | 0 241 178 A1 | 10/1987 | |
| EP | 0219762 B1 | 12/1990 | |
| EP | 0259749 B1 | 8/1991 | |
| EP | 200508 | 10/1991 | |
| EP | 273069 | 10/1992 | |
| EP | 0 514 691 | 11/1992 | |
| EP | 0250187 B1 | 9/1993 | |
| EP | 0452446 B1 | 12/1993 | |
| EP | 381194 | 8/1994 | |
| EP | 1 110 546 | 6/2001 | |
| EP | 1110546 A1 * | 6/2001 | |
| WO | WO 91/05540 A1 | 5/1991 | |
| WO | WO 92/15289 A1 | 9/1992 | |

| | | |
|---|---|---|
| WO | WO 95/05416 A2 | 2/1995 |
| WO | WO 95/18046 A1 | 7/1995 |
| WO | WO 00/18365 | 4/2000 |
| WO | WO 00/42992 | 7/2000 |
| WO | WO 01/70194 | 9/2001 |
| WO | WO 01/91721 | 12/2001 |

OTHER PUBLICATIONS

Lazaridou et al.; Thermophysical properties of chitosan, chitosan-starch and chitosan-pullulan films near the glass transition; Elsevier Science Ltd.; 2002; pp. 179-190.

* cited by examiner

THIN FILM WITH NON-SELF-AGGREGATING UNIFORM HETEROGENEITY AND DRUG DELIVERY SYSTEMS MADE THEREFROM

This application claims the benefit of U.S. Provisional Application No. 60/328,868, filed on Oct 12, 2001.

FIELD OF THE INVENTION

The invention relates to rapidly dissolving films and methods of their preparation. The films may also contain an active ingredient that is evenly distributed throughout the film. The even or uniform distribution is achieved by controlling one or more parameters, and particularly the drying process that reduces aggregation or conglomeration of the components in the film as it forms into a solid structure.

BACKGROUND OF THE RELATED TECHNOLOGY

Active ingredients such as drugs or pharmaceuticals, may be prepared in a tablet form to allow for accurate and consistent dosing. However, this form of preparing and dispensing medications has many disadvantages including that a large proportion of adjuvants that must be added to obtain a size able to be handled, that a larger medication form requires additional storage space, and that dispensing includes counting the tablets which has a tendency for inaccuracy. In addition, many persons, estimated to be as much as 28% of the population, have difficulty swallowing tablets. While tablets may be broken into smaller pieces or even crushed as a means of overcoming swallowing difficulties, this is not a suitable solution for many tablet or pill forms. For example, crushing or destroying the tablet or pill form to facilitate ingestion, alone or in admixture with food, may also destroy the controlled release properties.

As an alternative to tablets and pills, films may be used to carry active ingredients such as drugs, pharmaceuticals, and the like. However, historically films and the process of making drug delivery systems therefrom have suffered from a number of unfavorable characteristics that have not allowed them to be used in practice.

Films that incorporate a pharmaceutically active ingredient are disclosed in expired U.S. Pat. No. 4,136,145 to Fuchs, et al. ("Fuchs"). These films may be formed into a sheet, dried and then cut into individual doses. The Fuchs disclosure alleges the fabrication of a uniform film, which includes the combination of water-soluble polymers, surfactants, flavors, sweeteners, plasticizers and drugs. These allegedly flexible films are disclosed as being useful for oral, topical or enteral use. Examples of specific uses disclosed by Fuchs includes application of the films to mucosal membrane areas of the body, including the mouth, rectal, vaginal, nasal and ear areas.

Examination of films made in accordance with the process disclosed in Fuchs, however, reveals that such films suffer from the aggregation or conglomeration of particles, i.e., self-aggregation, making them inherently non-uniform. This result can be attributed to Fuchs' process parameters, which although not disclosed likely include the use of relatively long drying times, thereby facilitating intermolecular attractive forces, convection forces, air flow and the like to form such agglomeration.

The formation of agglomerates randomly distributes the film components and any active present as well. When large dosages are involved, a small change in the dimensions of the film would lead to a large difference in the amount of active per film. If such films were to include low dosages of active, it is possible that portions of the film may be substantially devoid of any active. Since sheets of film are usually cut into unit doses, certain doses may therefore be devoid of or contain an insufficient amount of active for the recommended treatment. Failure to achieve a high degree of accuracy with respect to the amount of active ingredient in the cut film can be harmful to the patient. For this reason, dosage forms formed by processes such as Fuchs, would not likely meet the stringent FDA standards relating to the variation of active in dosage forms. Currently, by law, dosage forms may not vary more than 10% in the amount of active present. When applied to dosage units based on films, this virtually mandates that uniformity in the film be present.

The problems of self-aggregation leading to non-uniformity of a film were addressed in U.S. Pat. No. 4,849,246 to Schmidt ("Schmidt"). Schmidt specifically pointed out that the methods disclosed by Fuchs did not provide a uniform film and recognized that that the creation of a non-uniform film necessarily prevents accurate dosing, which as discussed above is especially important in the pharmaceutical area. Schmidt abandoned the idea that a mono-layer film, such as described by Fuchs, may provide an accurate dosage form and instead attempted to solve this problem by forming a multi-layered film. Moreover, his process is a multi-step process that adds expense and complexity and is not practical for commercial use.

Other U.S. Patents directly addressed the problems of particle self-aggregation and non-uniformity inherent in conventional film forming techniques. In one attempt to overcome non-uniformity, U.S. Pat. No. 5,629,003 to Horstmann et al. and U.S. Pat. No. 5,948,430 to Zerbe et al. incorporated additional ingredients, i.e. gel formers and polyhydric alcohols respectively, to increase the viscosity of the film prior to drying in an effort to reduce aggregation of the components in the film. These methods have the disadvantage of requiring additional components, which translates to additional cost and manufacturing steps. Furthermore, both methods employ the use the conventional time-consuming drying methods such as a high-temperature air-bath using a drying oven, drying tunnel, vacuum drier, or other such drying equipment. The long length of drying time aids in promoting the aggregation of the active and other adjuvant, notwithstanding the use of viscosity modifiers. Such processes also run the risk of exposing the active, i.e., a drug, or vitamin C, or other components to prolonged exposure to moisture and elevated temperatures, which may render it ineffective or even harmful.

In addition to the concerns associated with degradation of an active during extended exposure to moisture, the conventional drying methods themselves are unable to provide uniform films. The length of heat exposure during conventional processing, often referred to as the "heat history", and the manner in which such heat is applied, have a direct effect on the formation and morphology of the resultant film product. Uniformity is particularly difficult to achieve via conventional drying methods where a relatively thicker film, which is well-suited for the incorporation of a drug active, is desired. Thicker uniform films are more difficult to achieve because the surfaces of the film and the inner portions of the film do not experience the same external conditions simultaneously during drying. Thus, observation of relatively thick films made from such conventional processing shows a non-uniform structure caused by convection and intermolecular forces and requires greater than 10% moisture to remain flexible. The amount of free moisture can often interfere over time with the drug leading to potency issues and therefore inconsistency in the final product.

Conventional drying methods generally include the use of forced hot air using a drying oven, drying tunnel, and the like. The difficulty in achieving a uniform film is directly related to the rheological properties and the process of water evaporation in the film-forming composition. When the surface of an aqueous polymer solution is contacted with a high temperature air current, such as a film-forming composition passing through a hot air oven, the surface water is immediately evaporated forming a polymer film or skin on the surface. This seals the remainder of the aqueous film-forming composition beneath the surface, forming a barrier through which the remaining water must force itself as it is evaporated in order to achieve a dried film. As the temperature outside the film continues to increase, water vapor pressure builds up under the surface of the film, stretching the surface of the film, and ultimately ripping the film surface open allowing the water vapor to escape. As soon as the water vapor has escaped, the polymer film surface reforms, and this process is repeated, until the film is completely dried. The result of the repeated destruction and reformation of the film surface is observed as a "ripple effect" which produces an uneven, and therefore non-uniform film. Frequently, depending on the polymer, a surface will seal so tightly that the remaining water is difficult to remove, leading to very long drying times, higher temperatures, and higher energy costs.

Other factors, such as mixing techniques, also play a role in the manufacture of a pharmaceutical film suitable for commercialization and Federal approval. Air is generally trapped in the composition during the mixing process, which can leave voids as the moisture evaporates during the drying stage. The results is non-uniformity in the final film product.

Therefore, there is a need for methods and compositions for film products, which use a minimal number of materials or components, and which provide a substantially non-self-aggregating uniform heterogeneity throughout the area of the films. Desirably, such films are produced through a selection of a polymer or combination of polymers that will provide a desired viscosity, a film-forming process such as reverse roll coating, and a controlled, and desirably rapid, drying process which serves to maintain the uniform distribution of non-self-aggregated components without the necessary addition of gel formers or polyhydric alcohols and the like which appear to be required in the products and for the processes of prior patents, such as the aforementioned Horstmann and Zerbe patents.

SUMMARY OF THE INVENTION

In one aspect of the present invention, there is provided a film and a method of forming same which can be divided into equally sized dosage units having substantially equal amounts of each compositional component present. This advantage is particularly useful because it permits large area films to be initially formed, and subsequently cut into individual dosage units without concern for whether each unit is compositionally equal. For example, the films of the present invention have particular applicability as pharmaceutical dosage delivery systems because each dosage unit, e.g., each individual dosage film unit, will contain the proper amount of drug. Pharmaceutical film dosage forms to date have not been marketed largely due to the inability to achieve this result.

In a further aspect of the present invention, there is provided a film product that is formed by combining a polymer and a polar solvent, forming the combination into a film, and drying the film in a controlled manner, desirably by initially only applying heat to the bottom side of the film, in order to maintain a non-self-aggregating uniform heterogeneity. Desirably, during the initial bottom drying stage, substantially no convection currents, i.e. hot air currents, are permitted to travel across the tops of the films. Once the visco-elastic properties of the film are such that the film components are "locked" in place and cannot move to cause non-uniformity, other methods of heating may then be employed. The polar solvent may be water, a polar organic solvent, or a combination thereof. An active ingredient may be added to the polymer and water combination prior to the drying step. Alternatively, or in addition to controlling the drying the film, the polymer may be selected in order to provide a viscosity that maintains the non-self-aggregating uniform heterogeneity. Moreover, the composition desirably is mixed in a manner to minimize the incorporation of air into the mixture and is desirably deaerated, such as by conditioning at room temperature, vacuum treatment or the like, to allow trapped air to escape prior to the drying process. This serves to eliminate bubble and void formation in the final film product, thereby further improving uniformity. Reverse roll is one particularly useful coating technique may also be used to form the film.

In another aspect of the invention, there is a process for preparing a film with a substantially uniform distribution of components. The process includes the steps of combining a polymer component and water to form a uniformly distributed matrix. This matrix is then formed into a film and fed onto the top side of a substrate surface having top and bottom sides. Heat is applied to the bottom side of the substrate surface in order to dry the film. The matrix from which the film is formed may also include an active ingredient. Also, either alternatively, or in addition to the particular method used to dry the film, the polymer may be selected in order to provide a viscosity that maintains the non-self-aggregating uniform heterogeneity. Reverse roll coating technique may also be used to form the film.

A further aspect of the present invention is a method of orally administering an active including the steps of:
(a) preparing a film by the steps of:
   (i) combining a polymer, an active component, and water to form a material with a non-self-aggregating uniform heterogeneity;
   (ii) forming the material into a film; and
   (iii) drying the film in a controlled manner to maintain the non-self-aggregating uniform heterogeneity; and
(b) introducing the film to the oral cavity of a mammal.

An even further aspect of the present invention is method of introducing an active component to liquid including the steps of:
(a) preparing a film by the steps of:
   (i) combining a polymer, an active component, and water to form a material with a non-self-aggregating uniform heterogeneity;
   (ii) forming the material into a film; and
   (iii) drying the film in a controlled manner to maintain the non-self-aggregating uniform heterogeneity; and
(b) placing the film into a liquid; and
(c) allowing the film to dissolve.

A still further aspect of the present invention provides a dosage form for the administration of an active including:
(a) a first layer including a film formed by the steps of:
   (i) combining a polymer, an active component, and water to form a material with a non-self-aggregating uniform heterogeneity;
   (ii) forming said material into a film; and
   (iii) drying said film in a controlled manner to maintain said non-self-aggregating uniform heterogeneity; and
(b) a substantially non-water soluble second layer.

Another aspect of the present invention provides a method of preparing a dosage form for the administration of an active including the steps of:
(a) combining a polymer, an active component, and water to form a material with a non-self-aggregating uniform heterogeneity;
(b) forming the material into a film;
(c) applying the film to a substantially non-water soluble support; and
(d) drying the film in a controlled manner to maintain the non-self-aggregating uniform heterogeneity.

In still another aspect of the present invention there is provided another method of administering an active including the steps of:
(a) preparing dosage form by the steps of:
  (i) combining a polymer, an active component, and water to form a material with a non-self-aggregating uniform heterogeneity;
  (ii) forming the material into a film;
  (iii) applying the film to a substantially non-water soluble support; and
  (iv) drying the film in a controlled manner to maintain the non-self-aggregating uniform heterogeneity;
(b) removing the film from said support; and
(c) applying the film to the oral cavity of a mammal.

Another aspect of the invention provides a film product formed by the steps of:
(a) combining a polymer and a liquid carrier to form a material with a non-self-aggregating uniform heterogeneity;
(b) forming said material into a film; and
(c) removing said liquid carrier, for example, by evaporative methods or by permitting volatilization to occur at selected temperatures, from said film in a manner to maintain said non-self-aggregating uniform heterogeneity.

Also provided is a process for making a film having a substantially uniform distribution of components including:
(a) combining a polymer component and liquid carrier to form a matrix with a uniform distribution of said components;
(b) forming a film from said matrix; and
(c) removing said liquid carrier, for example, by evaporative methods or by permitting volatilization to occur at selected temperatures, from said film in a manner to maintain said uniform distribution.

A still further aspect of the present invention provides process for making a film having a substantially uniform distribution of components including:
(a) combining a polymer component and a polar solvent to form a matrix with a uniform distribution of said components, said polymer selected to provide a viscosity sufficient to maintain said uniform distribution; and
(b) forming a film from said matrix.

The invention also includes films and a process for preparing films having a substantially uniform distribution of components. The process includes the steps of combining a polymer component and water to form a uniformly distributed matrix. This matrix is then formed into a film and fed onto a substrate surface having top and bottom sides where the bottom side is in substantially uniform contact with a bottom drying medium, such as a water bath or heated air space controlled at a temperature sufficient to dry the film. Desirably, no external air currents or heat is applied directly to the exposed top surface of the film during the drying process until the film structure has solidified sufficiently to prevent flow, migration and intermolecular attractive forces from creating aggregates or conglomerates. Desirably the heat is controllably conducted by the substrate surface to the film to effectuate drying. The matrix from which the film is formed may also include an active ingredient. Also, either alternatively, or in addition to rapidly drying the film, the polymer may be selected in order to provide a viscosity that maintains the non-self-aggregating uniform heterogeneity.

A pharmaceutical and/or cosmetic dosage form is also provided that includes a film having a uniformly dispersed composition including a polymer, a pharmaceutical and/or cosmetic active and a solvent, said film being formed by depositing a wet film of said composition onto a substrate surface and controllably drying the wet film from the side contacting the substrate to prevent self-aggregation and achieve compositional uniformity.

A still further aspect of the present invention includes a pharmaceutical and/or cosmetic dosage form including a polymeric film having no more than a 10% variance of a pharmaceutical and/or cosmetic active per unit area.

The present invention also provides a pharmaceutical composition in the form of a film for external or topical administration, including a composition having a uniformly distributed combination of a polymer, a polar solvent, and a pharmaceutical active, said composition in its dried film form maintaining the uniform distribution of components through the application of controlled bottom drying of the film.

A pharmaceutical dispenser is also provided that includes individual unit dosage forms of the pharmaceutical compositions and films of the present invention. The dosage forms may be optionally stacked in a dispenser or in a roll.

DETAILED DESCRIPTION OF THE INVENTION

Figure 1:
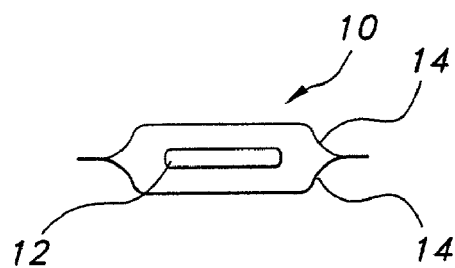
FIG. 1 shows a side view of a package containing a unit dosage film of the present invention.
Figure 2:
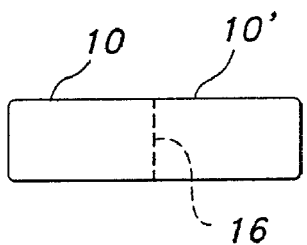
FIG. 2 shows a top view of two adjacently coupled packages containing individual unit dosage forms of the present invention, separated by a tearable perforation.

For the purposes of the present invention the term non-self-aggregating uniform heterogeneity refers to the ability of the films of the present invention, which are formed from one or more components in addition to a polar solvent, to provide a substantially reduced occurrence of, i.e. little or no, aggregation or conglomeration of components within the film as is normally experienced when films are formed by conventional drying methods such as a high-temperature air-bath using a drying oven, drying tunnel, vacuum drier, or other such drying equipment. The term heterogeneity, as used in the present invention, includes films that will incorporate a single component, such as a polymer, as well as combinations of components, such as a polymer and an active. Uniform heterogeneity includes the substantial absence of aggregates or conglomerates as is common in conventional mixing and heat drying methods used to form films.

Furthermore, the films of the present invention have a substantially uniform thickness, which is also not provided by the use of conventional drying methods used for drying water-based polymer systems. The absence of a uniform thickness detrimentally affects uniformity of component distribution throughout the area of a given film.

The film products of the present invention are produced by a combination of a properly selected polymer and a polar solvent, optionally including an active ingredient as well as other fillers known in the art. These films provide a non-self-aggregating uniform heterogeneity of the components within them by utilizing a selected casting or deposition method and a controlled drying process. Examples of controlled drying processes include, but are not limited to, the use of the apparatus disclosed in U.S. Pat. No. 4,631,837 to Magoon ("Magoon"), herein incorporated by reference, as well as hot air impingement across the bottom substrate and bottom heating plates. Another drying technique for obtaining the films of the present invention is controlled radiation drying in the absence of air currents, such as infrared and radio frequency radiation (i.e. microwaves).

The objective of the drying process is to provide a method of drying the films that avoids complications, such as the noted "rippling" effect, that are associated with conventional drying methods and which initially dry the upper surface of the film, trapping moisture inside. In conventional oven drying methods, as the moisture trapped inside subsequently evaporates, the top surface is altered by being ripped open and then reformed. These complications are avoided by the present invention, and a uniform film is provided by drying the bottom surface of the film first or otherwise preventing the formation of polymer film formation (skin) on the top surface of the film prior to drying the depth of the film. This may be achieved by applying heat to the bottom surface of the film with substantially no top air flow, or alternatively by the introduction of controlled microwaves to evaporate the water or other polar solvent within the film, again with substantially no top air flow. The humidity level of the area surrounding the top surface may also be appropriately adjusted to prevent premature closure or skinning of the polymer surface.

This manner of drying the films provides several advantages. Among these are the faster drying times and a more uniform surface of the film, as well as uniform distribution of components for any given area in the film. In addition, the faster drying time allows viscosity to quickly build within the film, further encouraging a uniform distribution of components and decrease in aggregation of components in the final film product. Desirably, the drying of the film will occur within about ten minutes or fewer, or more desirably within about five minutes or fewer.

The present invention yields exceptionally uniform film products when attention is paid to reducing the aggregation of the compositional components. By avoiding the introduction of and eliminating excessive air in the mixing process, selecting polymers and solvents to provide a controllable viscosity and by drying the film in a rapid manner from the bottom up, such films result.

The products and processes of the present invention rely on the interaction among various steps of the production of the films in order to provide films that substantially reduce the self-aggregation of the components within the films. Specifically, these steps include the particular method used to form the film, making the composition mixture to prevent air bubble inclusions, controlling the viscosity of the film forming composition and the method of drying the film. More particularly, a greater viscosity of components in the mixture is particularly useful when the active is not soluble in the selected polar solvent in order to prevent the active from settling out. However, the viscosity must not be too great as to hinder or prevent the chosen method of casting, which desirably includes reverse roll coating due to its ability to provide a film of substantially consistent thickness.

While the viscosity and casting method are important in the first steps of forming the film to promote uniformity, the method of drying is also important. Although the viscosity assists uniformity initially, a rapid drying process ensures that the uniformity will be maintained until the film is dry. A number of techniques may be employed in the mixing stage to prevent bubble inclusions in the final film. To provide a composition mixture with substantially no air bubble formation in the final product, anti-foaming or surface-tension reducing agents are employed. Additionally, the speed of the mixture is desirably controlled to prevent cavitation of the mixture in a manner which pulls air into the mix. Finally, air bubble reduction can further be achieved by allowing the mix to stand for a sufficient time for bubbles to escape prior to drying the film.

When the matrix is formed including the film-forming polymer and polar solvent in addition to any additives and the active ingredient, this may be done in a number of steps. For example, the ingredients may all be added together or a pre-mix may be prepared. The advantage of a pre-mix is that all ingredients except for the active may be combined in advance, with the active added just prior to formation of the film. This is especially important for actives that may degrade with prolonged exposure to water, air or another polar solvent.

Figure 6:
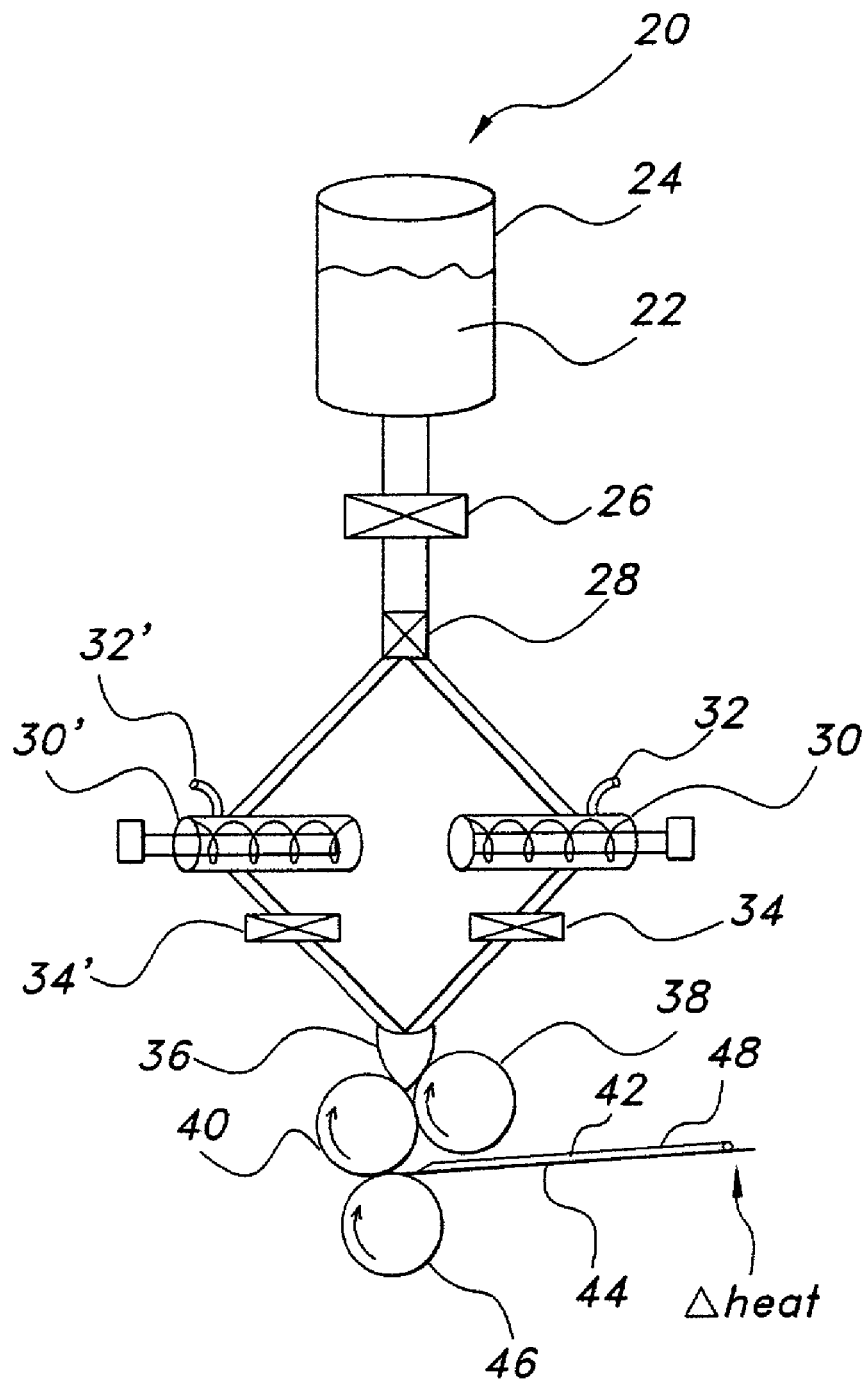
FIG. 6 is a schematic view of an apparatus suitable for preparation of a pre-mix, addition of an active, and subsequent formation of the film.

FIG. 6 shows an apparatus 20 suitable for the preparation of a pre-mix, addition of an active and subsequent formation of a film. The pre-mix or master batch 22, which includes the film-forming polymer, polar solvent, and any other additives except a drug active is added to the master batch feed tank 24. Then a pre-determined amount of the master batch is controllably fed via a first metering pump 26 and control valve 28 to either or both of the first and second mixers, 30, 31'. The required amount of the drug is added to the desired mixer through an opening in each of the mixers, 32, 32'. After the drug has been blended with the master batch pre-mix for a sufficient time to provide a uniform matrix, a specific amount of the uniform matrix is then fed to the pan 36 through the second metering pumps, 34, 34'. The metering roller 38 determines the thickness of the film 42 and applies it to the application roller 40. The film 42 is finally formed on the substrate 44 and carried away via the support roller 46. The wet film is then dried using controlled bottom drying, desirably in the absence of external air currents or heat on the top (exposed) surface of the film 48 as described herein.

Monitoring and control of the thickness of the film also contributes to the production of a uniform film by providing a film of uniform thickness. The thickness of the film may be monitored with gauges such as Beta Gauges. A gauge may be coupled to another gauge at the end of the drying apparatus, i.e. drying oven or tunnel, to communicate through feedback loops to control and adjust the opening in the coating apparatus, resulting in control of uniform film thickness.

The film products are generally formed by combining a properly selected polymer and polar solvent, as well as any active ingredient or filler as desired. Desirably, the solvent content of the combination is at least about 30% by weight of the total combination. The matrix formed by this combination is formed into a film, desirably by roll coating, and then dried, desirably by a rapid and controlled drying process to maintain the uniformity of the film, more specifically, a non-self-aggregating uniform heterogeneity. The resulting film will desirably contain less than about 10% by weight solvent, more desirably less than about 8% by weight solvent, even more desirably less than about 6% by weight solvent and most desirably less than about 2%. The solvent may be water, a polar organic solvent including, but not limited to, ethanol, isopropanol, acetone, methylene chloride, or any combination thereof.

Film-Forming Polymers

The polymer may be water soluble, water insoluble, or a combination of one or more either water soluble or water insoluble polymers. The polymer may include cellulose or a cellulose derivative. Specific examples of useful water soluble polymers include, but are not limited to, pullulan, hydroxypropylmethyl cellulose, hydroxyethyl cellulose, hydroxypropyl cellulose, polyvinyl pyrrolidone, carboxymethyl cellulose, polyvinyl alcohol, sodium aginate, polyethylene glycol, xanthan gum, tragancanth gum, guar gum, acacia gum, arabic gum, polyacrylic acid, methylmethacrylate copolymer, carboxyvinyl copolymers, starch, and combinations thereof. Specific examples of useful water insoluble polymers include, but are not limited to, ethyl cellulose, hydroxypropyl ethyl cellulose, cellulose acetate phthalate, hydroxypropyl methyl cellulose phthalate and combinations thereof.

Other polymers useful for incorporation into the films of the present invention include biodegradable polymers, copolymers, block polymers and combinations thereof. Among the known useful polymers or polymer classes which meet the above criteria are: poly(glycolic acid) (PGA), poly (lactic acid) (PLA), polydioxanoes, polyoxalates, poly($\alpha$-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and poly(lactic acid), copolymers of polyurethane and poly(lactic acid), copolymers of $\alpha$-amino acids, copolymers of $\alpha$-amino acids and caproic acid, copolymers of $\alpha$-benzyl glutamate and polyethylene glycol, copolymers of succinate and poly (glycols), polyphosphazene, polyhydroxy-alkanoates and mixtures thereof. Binary and ternary systems are contemplated.

Other specific polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100L, believed to be 100% lactide having a melting point within the range of 338°-347° F. (170°-175° C.); lactide/glycolide 100L, believed to be 100% glycolide having a melting point within the range of 437°-455° F. (225°-235° C.); lactide/glycolide 85/15, believed to be 85% lactide and 15% glycolide with a melting point within the range of 338°-347° F. (170°-175° C.); and lactide/glycolide 50/50, believed to be a copolymer of 50% lactide and 50% glycolide with a melting point within the range of 338°-347° F. (170°-175° C).

The Biodel materials represent a family of various polyanhydrides which differ chemically.

Although a variety of different polymers may be used, it is desired to select polymers to provide a desired viscosity of the mixture prior to drying. For example, if the active or other components are not soluble in the selected solvent, a polymer that will provide a greater viscosity is desired to assist in maintaining uniformity. On the other hand, if the components are soluble in the solvent, a polymer that provides a lower viscosity may be preferred.

The polymer plays an important role in affecting the viscosity of the film. Viscosity is one property of a liquid that controls the stability of the active in an emulsion, a colloid or a suspension. Generally the viscosity of the matrix will vary from about 400 cps to about 100,000 cps, preferably from about 800 cps to about 60,000 cps, and most preferably from about 1,000 cps to about 40,000 cps. Desirably, the viscosity of the film-forming matrix will rapidly increase upon initiation of the drying process.

The viscosity may be adjusted based on the selected active depending on the other components within the matrix. For example, if the component is not soluble within the selected solvent, a proper viscosity may be selected to prevent the component from settling which would adversely affect the uniformity of the resulting film. The viscosity may be adjusted in different ways. To increase viscosity of the film matrix, the polymer may be chosen of a higher molecular weight or crosslinkers may be added, such as salts of calcium, sodium and potassium. The viscosity may also be adjusted by adjusting the temperature or by adding a viscosity increasing component. Components that will increase the viscosity or stabilize the emulsion/suspension include higher molecular weight polymers and polysaccharides and gums, which include without limitation, alginate, carrageenan, hydroxypropyl methyl cellulose, locust bean gum, guar gum, xanthan gum, dextran, gum arabic, gellan gum and combinations thereof.

Controlled Release Films

The term "controlled release" is intended to mean the release of active at a preselected or desired rate. This rate will vary depending upon the application. Desirable rates include fast or immediate release profiles as well as delayed, sustained or sequential release. Combinations of release patterns, such as initial spiked release followed by lower levels of sustained release of active are contemplated.

The polymers that are chosen for the films of the present invention may also be chosen to allow for controlled disintegration of the active. This may be achieved by providing a substantially water insoluble film that incorporates an active that will be released from the film over time. This may be accomplished by incorporating a variety of different soluble or insoluble polymers and may also include biodegradable polymers in combination. Alternatively, coated controlled release active particles may be incorporated into a readily soluble film matrix to achieve the controlled release property of the active inside the digestive system upon consumption.

Films that provide a controlled release of the active are particularly useful for buccal, gingival, and sublingual applications.

The convenience of administering a single dose of a medication which releases active ingredients in a controlled fashion over an extended period of time as opposed to the administration of a number of single doses at regular intervals has long been recognized in the pharmaceutical arts. The advantage to the patient and clinician in having consistent and uniform blood levels of medication over an extended period of time are likewise recognized. The advantages of a variety of sustained release dosage forms are well known. However, the preparation of a film that provides the controlled release of an active has advantages in addition to those well-known for controlled release tablets. For example, thin films are difficult to inadvertently aspirate and provide an increased patient compliance because they need not be swallowed like a tablet. Moreover, certain embodiments of the inventive films are designed to adhere to the buccal cavity and tongue, where they controllably dissolve. Furthermore, thin films may not be crushed in the manner of controlled release tablets which is a problem leading to abuse of drugs such as Oxycontin.

The actives employed in the present invention may be incorporated into the film compositions of the present invention in a controlled release form. For example, particles of drug may be coated with polymers such as ethyl cellulose or polymethacrylate, commercially available under brand names such as Aquacoat ECD and Eudragit E-100, respectively. Solutions of drug may also be absorbed on such polymer materials and incorporated into the inventive film compositions. Other components such as fats and waxes, as well as sweeteners and/or flavors may also be employed in such controlled release compositions.

Actives

When an active is introduced to the film, the amount of active per unit area is determined by the uniform distribution of the film. For example, when the films are cut into individual dosage forms, the amount of the active in the dosage form can be known with a great deal of accuracy. This is achieved because the amount of the active in a given area is substantially identical to the amount of active in an area of the same dimensions in another part of the film. The accuracy in dosage is particularly advantageous when the active is a medicament, i.e. a drug.

The active components that may be incorporated into the films of the present invention include, without limitation pharmaceutical and cosmetic actives, drugs, medicaments, mouthwash components, flavors, fragrances, enzymes, preservatives, sweetening agents, colorants, spices, vitamins and combinations thereof A wide variety of medicaments and pharmaceutical compositions may be included in the dosage forms of the present invention. Examples of useful drugs include ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

Examples of medicating active ingredients contemplated for use in the present invention include antacids, $H_2$-antagonists, and analgesics. For example, antacid dosages can be prepared using the ingredients calcium carbonate alone or in combination with magnesium hydroxide, and/or aluminum hydroxide Moreover, antacids can be used in combination with $H_2$-antagonists.

Analgesics include opiates and opiate derivatives, such as Oxycontin, ibuprofen, aspirin, acetaminophen, and combinations thereof that may optionally include caffeine.

Other preferred drugs for other preferred active ingredients for use in the present invention include anti-diarrheals such as immodium AD, anti-histamines, anti-tussives, decongestants, vitamins, and breath fresheners. Also contemplated for use herein are anxiolytics such as Xanax; anti-psychotics such as clozaril and Haldol; non-steroidal anti-inflammatories (NSAID's) such as Voltaren and Lodine, anti-histamines such as Claritin, Hismanal, Relafen, and Tavist; anti-emetics such as Kytril and Cesamet; bronchodilators such as Bentolin, Proventil; anti-depressants such as Prozac, Zoloft, and Paxil; anti-migraines such as Imigra, ACE-inhibitors such as Vasotec, Capoten and Zestril; anti-Alzheimer's agents, such as Nicergoline; and $Ca^H$-antagonists such as Procardia, Adalat, and Calan.

The popular $H_2$-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

An anti-oxidant may also be added to the film to prevent the degradation of an active, especially where the active is photosensitive.

Cosmetic active agents may include breath freshening compounds like menthol, other flavors or fragrances, especially those used for oral hygiene, as well as actives used in dental and oral cleansing such as quaternary ammonium bases. The effect of flavors may be enhanced using flavor enhancers like tartaric acid, citric acid, vanillin, or the like.

Also color additives can be used in preparing the films. Such color additives include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

Other examples of coloring agents include known azo dyes, organic or inorganic pigments, or coloring agents of natural origin. Inorganic pigments are preferred, such as the oxides or iron or titanium, these oxides, being added in concentrations ranging from about 0.001 to about 10%, and preferably about 0.5 to about 3%, based on the weight of all the components.

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. A non-limiting representative list of examples includes mint oils, cocoa, and citrus oils such as lemon, orange, grape, lime and grapefruit and fruit essences including apple, pear, peach, grape, strawberry, raspberry, cherry, plum, pineapple, apricot or other fruit flavors.

The flavorings may be added to provide a hot or cold flavored drink or soup. These flavorings include, without limitation, tea and soup flavorings such as beef and chicken.

Other useful flavorings include aldehydes and esters such as benzaldehyde (cherry, almond), citral i.e., alphacitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanol (green fruit), and 2-dodecenal (citrus, mandarin), combinations thereof and the like.

The sweeteners may be chosen from the following non-limiting list: glucose (corn syrup), dextrose, invert sugar, fructose, and combinations thereof; saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof, and natural intensive sweeteners, such as Lo Han Kuo. Other sweeteners may also be used.

When the active is combined with the polymer in the solvent, the type of matrix that is formed depends on the solubilities of the active and the polymer. If the active and/or polymer are soluble in the selected solvent, this may form a solution. However, if the components are not soluble, the matrix may be classified as an emulsion, a colloid, or a suspension.

Dosages

The film products of the present invention are capable of accommodating a wide range of amounts of the active ingredient. The films are capable of providing an accurate dosage amount (determined by the size of the film and concentration of the active in the original polymer/water combination) regardless of whether the required dosage is high or extremely low. Therefore, depending on the type of active or pharmaceutical composition that is incorporated into the film, the active amount may be as high as about 300 mg, desirably up to about 150 mg or as low as the microgram range, or any amount therebetween.

The film products and methods of the present invention are well suited for high potency, low dosage drugs. This is accomplished through the high degree of uniformity of the films. Therefore, low dosage drugs, particularly more potent racemic mixtures of actives are desirable.

Optional Components

A variety of other components and fillers may also be added to the films of the present invention. These may include, without limitation, surfactants; plasticizers which assist in compatibilizing the components within the mixture; polyalcohols; anti-foaming agents, such as silicone-containing compounds, which promote a smoother film surface by releasing oxygen from the film; and thermo-setting gels such as pectin, carageenan, and gelatin, which help in maintaining the dispersion of components.

The variety of additives that can be incorporated into the inventive compositions may provide a variety of different functions. Examples of classes of additives include excipients, lubricants, buffering agents, stabilizers, blowing agents, pigments, coloring agents, fillers, bulking agents, sweetening agents, flavoring agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof. These additives may be added with the active ingredient(s).

Useful additives include, for example, gelatin, vegetable proteins such as sunflower protein, soybean proteins, cotton seed proteins, peanut proteins, grape seed proteins, whey proteins, whey protein isolates, blood proteins, egg proteins, acrylated proteins, water-soluble polysaccharides such as alginates, carrageenans, guar gum, agar-agar, xanthan gum, gellan gum, gum arabic and related gums (gum ghatti, gum karaya, gum tragancanth), pectin, water-soluble derivatives of cellulose: alkylcelluloses hydroxyalkylcelluloses and hydroxyalkylalkylcelluloses, such as methylcelulose, hydroxymethylcellulose, hydroxyethylcellulose, hydroxypropylcellulose, hydroxyethylmethylcellulose, hydroxypropyhnethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water-soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVY/vinyl acetate copolymer, and polycrotonic acids; also suitable are phthalated gelatin, gelatin succinate, crosslinked gelatin, shellac, water soluble chemical derivatives of starch, cationically modified acrylates and methacrylates possessing, for example, a tertiary or quaternary amino group, such as the diethylaminoethyl group, which may be quaternized if desired; and other similar polymers.

Such extenders may optionally be added in any desired amount desirably within the range of up to about 80%, desirably about 3% to 50% and more desirably within the range of 3% to 20% based on the weight of all components.

Further additives may be inorganic fillers, such as the oxides of magnesium aluminum, silicon, titanium, etc. desirably in a concentration range of about 0.02% to about 3% by weight and desirably about 0.02% to about 1% based on the weight of all components.

Further examples of additives are plasticizers which include polyalkylene oxides, such as polyethylene glycols, polypropylene glycols, polyethylene-propylene glycols, organic plasticizers with low molecular weights, such as glycerol, glycerol monoacetate, diacetate or triacetate, triacetin, polysorbate, cetyl alcohol, propylene glycol, sorbitol, sodium diethylsulfosuccinate, triethyl citrate, tributyl citrate, and the like, added in concentrations ranging from about 0.5% to about 30%, and desirably ranging from about 0.5% to about 20% based on the weight of the polymer.

There may further be added compounds to improve the flow properties of the starch material such as animal or vegetable fats, desirably in their hydrogenated form, especially those which are solid at room temperature. These fats desirably have a melting point of 50° C. or higher. Preferred are tri-glycerides with $C_{12}$-, $C_{14}$-, $C_{16}$-, $C_{18}$-, $C_{20}$- and $C_{22}$-fatty acids. These fats can be added alone without adding extenders or plasticizers and can be advantageously added alone or together with mono- and/or di-glycerides or phosphatides, especially lecithin. The mono- and di-glycerides are desirably derived from the types of fats described above, i.e. with $C_{12}$-, $C_{14}$-, $C_{16}$-, $C_{18}$-, $C_{20}$- and $C_{22}$-fatty acids.

The total amounts used of the fats, mono-, di-glycerides and/or lecithins are up to about 5% and preferably within the range of about 0.5% to about 2% by weight of the total composition.

It is further useful to add silicon dioxide, calcium silicate, or titanium dioxide in a concentration of about 0.02% to about 1% by weight of the total composition. These compounds act as texturizing agents.

These additives are to be used in amounts sufficient to achieve their intended purpose. Generally, the combination of certain of these additives will alter the overall release profile of the active ingredient and can be used to modify, i.e. impede or accelerate the release.

Lecithin is one surface active agent for use in the present invention. Lecithin can be included in the feedstock in an amount of from about 0.25% to about 2.00% by weight. Other surface active agents, i.e. surfactants, include, but are not limited to, cetyl alcohol, sodium lauryl sulfate, the Spans™ and Tweens™ which are commercially available from ICI Americas, Inc. Carbowax™ is yet another modifier which is very useful in the present invention. Tweens™ or combinations of surface active agents may be used to achieve the desired HLB.

As additional modifiers which enhance the procedure and product of the present invention are identified, Applicants intend to include all such additional modifiers within the scope of the invention claimed herein.

Other ingredients include binders which contribute to the ease of formation and general quality of the films. Non-limiting examples of binders include starches, pregelatinize starches, gelatin, polyvinylpyrrolidone, methylcellulose, sodium carboxymethylcellulose, ethylcellulose, polyacrylamides, polyvinyloxoazolidone, and polyvinylalcohols.

Forming the Film

The films of the present invention must be formed into a sheet prior to drying. After the desired components are combined to form a multi-component matrix, including the polymer, water, and an active or other components as desired, the combination is formed into a sheet or film, by any method known in the art such as extrusion, coating, spreading, casting or drawing the multi-component matrix. If a multi-layered film is desired, this may be accomplished by co-extruding more than one combination of components which may be of the same or different composition. A multi-layered film may also be achieved by coating, spreading, or casting a combination onto an already formed film layer.

Although a variety of different film-forming techniques may be used, it is desirable to select a method that will provide a flexible film, such as reverse roll coating. The flexibility of the film allows for the sheets of film to be rolled and transported for storage or prior to being cut into individual dosage forms. Desirably, the films will also be self-supporting or in other words able to maintain their integrity and structure in the absence of a separate support. Furthermore, the films of the present invention may be selected of materials that are edible or ingestible.

Coating or casting methods are particularly useful for the purpose of forming the films of the present invention. Specific examples include reverse roll coating, gravure coating, immersion or dip coating, metering rod or meyer bar coating, slot die or extrusion coating, gap or knife over roll coating, air knife coating, curtain coating, or combinations thereof, especially when a multi-layered film is desired.

Roll coating, or more specifically reverse roll coating, is particularly desired when forming films in accordance with the present invention. This procedure provides excellent control and uniformity of the resulting films, which is desired in the present invention. In this procedure, the coating material is measured onto the applicator roller by the precision setting of the gap between the upper metering roller and the application roller below it. The coating is transferred from the application roller to the substrate as it passes around the support roller adjacent to the application roller. Both three roll and four roll processes are common.

The gravure coating process relies on an engraved roller running in a coating bath, which fills the engraved dots or lines of the roller with the coating material. The excess coating on the roller is wiped off by a doctor blade and the coating is then deposited onto the substrate as it passes between the engraved roller and a pressure roller.

Offset Gravure is common, where the coating is deposited on an intermediate roller before transfer to the substrate.

In the simple process of immersion or dip coating, the substrate is dipped into a bath of the coating, which is normally of a low viscosity to enable the coating to run back into the bath as the substrate emerges.

In the metering rod coating process, an excess of the coating is deposited onto the substrate as it passes over the bath roller. The wire-wound metering rod, sometimes known as a Meyer Bar, allows the desired quantity of the coating to remain on the substrate. The quantity is determined by the diameter of the wire used on the rod.

In the slot die process, the coating is squeezed out by gravity or under pressure through a slot and onto the substrate. If the coating is 100% solids, the process is termed "Extrusion" and in this case, the line speed is frequently much faster than the speed of the extrusion. This enables coatings to be considerably thinner than the width of the slot.

The gap or knife over roll process relies on a coating being applied to the substrate which then passes through a "gap" between a "knife" and a support roller. As the coating and substrate pass through, the excess is scraped off.

Air knife coating is where the coating is applied to the substrate and the excess is "blown off" by a powerful jet from the air knife. This procedure is useful for aqueous coatings.

In the curtain coating process, a bath with a slot in the base allows a continuous curtain of the coating to fall into the gap between two conveyors. The object to be coated is passed along the conveyor at a controlled speed and so receives the coating on its upper face.

Drying the Film

The drying step can also be a contributing factor with regard to maintaining the uniformity of the film composition. A controlled drying process is particularly important when, in the absence of a viscosity increasing composition or a composition in which the viscosity is controlled, for example by the selection of the polymer, the components within the film may have an increased tendency to aggregate or conglomerate. An alternative method of forming a film with an accurate dosage, that would not necessitate the controlled drying process, would be to cast the films on a predetermined well. With this method, although the components may aggregate, this will not result in the migration of the active to an adjacent dosage form, since each well may define the dosage unit per se.

When a controlled or rapid drying process is desired, this may be through a variety of methods. A variety of methods may be used including those that require the application of heat. The liquid carriers are removed from the film in a manner such that the uniformity, or more specifically, the non-self-aggregating uniform heterogeneity, that is obtained in the wet film is maintained.

Desirably, the film is dried from the bottom of the film to the top of the film. Substantially no air flow is present across the top of the film during its initial setting period, during which a solid, visco-elastic structure is formed. This can take place within the first few minutes, e.g. about the first 0.5 to about 4.0 minutes of the drying process. Controlling the drying in this manner, prevents the destruction and reformation of the film's top surface, which results from conventional drying methods. This is accomplished by forming the film and placing it on the top side of a surface having top and bottom sides. Then, heat is initially applied to the bottom side of the film to provide the necessary energy to evaporate or otherwise remove the liquid carrier. The films dried in this manner dry more quickly and evenly as compared to air-dried films, or those dried by conventional drying means. In contrast to an air-dried film that dries first at the top and edges, the films dried by applying heat to the bottom dry simultaneously at the center as well as at the edges. This also prevents settling of ingredients that occurs with films dried by conventional means.

The temperature at which the films are dried is about 100° C. or less, desirably about 90° C. or less, and most desirably about 80° C. or less.

Another method of controlling the drying process, which may be used alone or in combination with other controlled methods as disclosed above includes controlling and modifying the humidity within the drying apparatus where the film is being dried. In this manner, the premature drying of the top surface of the film is avoided.

A specific example of an appropriate drying method is that disclosed by Magoon. Magoon is specifically directed toward a method of drying fruit pulp. However, the present inventors have adapted this process toward the preparation of thin films.

The method and apparatus of Magoon are based on an interesting property of water. Although water transmits energy by conduction and convection both within and to its surroundings, water only radiates energy within and to water. Therefore, the apparatus of Magoon includes a surface onto which the fruit pulp is placed that is transparent to infrared radiation. The underside of the surface is in contact with a temperature controlled water bath. The water bath temperature is desirably controlled at a temperature slightly below the boiling temperature of water. When the wet fruit pulp is placed on the surface of the apparatus, this creates a "refractance window." This means that infrared energy is permitted to radiate through the surface only to the area on the surface occupied by the fruit pulp, and only until the fruit pulp is dry. The apparatus of Magoon provides the films of the present invention with an efficient drying time reducing the instance of aggregation of the components of the film.

The films may initially have a thickness of about 500 μm to about 1,500 μm, or about 20 mils to about 60 mils, and when dried have a thickness from about 3 μm to about 250 μm, or about 0.1 mils to about 10 mils. Desirably, the dried films will have a thickness of about 2 mils to about 8 mils, and more desirably, from about 3 mils to about 6 mils.

Uses of Thin Films

The thin films of the present invention are well suited for many uses. The high degree of uniformity of the components of the film makes them particularly well suited for incorporating pharmaceuticals. Furthermore, the polymers used in construction of the films may be chosen to allow for a range of disintegration times for the films. A variation or extension in the time over which a film will disintegrate may achieve control over the rate that the active is released, which may allow for a sustained release delivery system. In addition, the films may be used for the administration of an active to any of several body surfaces, especially those including mucous membranes, such as oral, anal, vaginal, ophthalmological, the surface of a wound, either on a skin surface or within a body such as during surgery, and similar surfaces.

The films may be used to orally administer an active. This is accomplished by preparing the films as described above and introducing them to the oral cavity of a mammal. This film may be prepared and adhered to a second or support layer from which it is removed prior to use, i.e. introduction to the oral cavity. An adhesive may be used to attach the film to the support or backing material which may be any of those known in the art, and is preferably not water soluble. If an adhesive is used, it will desirably be a food grade adhesive that is ingestible and does not alter the properties of the active. Mucoadhesive compositions are particularly useful.

The films may be applied to the tongue of the mammal. When this is desired, a specific film shape, corresponding to the shape of the tongue may be preferred. Therefore the film may be cut to a shape where the side of the film corresponding to the back of the tongue will be longer than the side corresponding to the front of the tongue. Specifically, the desired shape may be that of a triangle or trapezoid. Desirably, the film will adhere to the oral cavity preventing it from being ejected from the oral cavity and permitting more of the active to be introduced to the oral cavity as the film dissolves.

Another use for the films of the present invention takes advantage of the films' tendency to dissolve quickly when introduce to a liquid. An active may be introduced to a liquid by preparing a film in accordance with the present invention, introducing it to a liquid, and allowing it to dissolve. This may be used either to prepare a liquid dosage form of an active, or to flavor a beverage.

Figure 3:
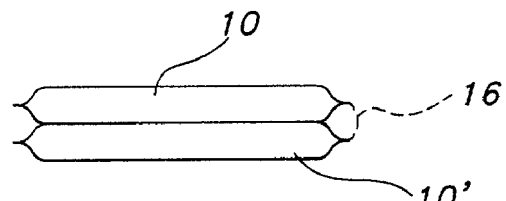
FIG. 3 shows a side view of the adjacently coupled packages of FIG. 2 arranged in a stacked configuration.
Figure 4:
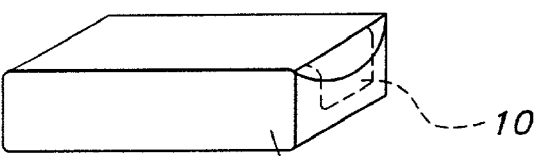
FIG. 4 shows a perspective view of a dispenser for dispensing the packaged unit dosage forms, dispenser containing the packaged unit dosage forms in a stacked configuration.
Figure 5:
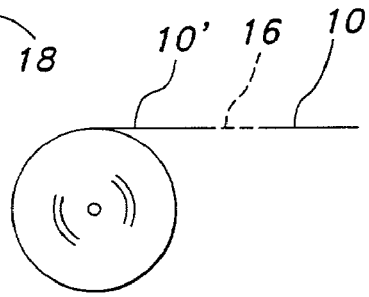
FIG. 5 is a schematic view of a roll of coupled unit dose packages of the present invention.

The films of the present invention are desirably packaged in sealed, air and moisture resistant packages to protect the active from exposure oxidation, hydrolysis, volatilization and interaction with the environment. Referring to FIG. 1, a packaged pharmaceutical dosage unit 10, includes each film 12 individually wrapped in a pouch or between foil and/or plastic laminate sheets. The pouches 10, 10' can be linked together with tearable or perforated joints 16 and packaged in a roll as in FIG. 5 or stacked as shown in FIG. 3 and sold in a dispenser 18 as shown in FIG. 4. The dispenser may contain a full supply of the medication typically prescribed for the intended therapy, but due to the thinness of the film and package, is smaller and more convenient than traditional bottles used for tablets, capsules and liquids. Moreover, the films of the present invention dissolve instantly upon contact with saliva or mucosal membrane areas, eliminating the need to wash the dose down with water.

Desirably, a series of such unit doses are packaged together in accordance with the prescribed regimen or treatment, e.g., a 10-90 day supply, depending on the particular therapy. The individual films can be packaged on a backing and peeled off for use.

The features and advantages of the present invention are more fully shown by the following examples which are provided for purposes of illustration, and are not to be construed as limiting the invention in any way.

EXAMPLES

Water soluble thin film compositions of the present invention are prepared using the amounts described in Table 1.

TABLE 1

| Ingredient | Weight (g) | | | | | | | | |
|---|---|---|---|---|---|---|---|---|---|
| | A | B | C | D | E | F | G | H | I |
| Hydroxypropylmethyl cellulose | | 1.76 | | 1.63 | 32.00 | | 3.67 | | 32.00 |
| Peppermint oil | | 0.90 | 1.0 | 1.05 | | 8.0 | 2.67 | | |
| Sweetener | 0.15 | 0.15 | 0.22 | 0.10 | | 4.6 | 1.53 | 0.15 | |
| Polyvinylpyrrolidone | | 0.94 | | 1.05 | | 7.0 | 2.33 | | |
| Tween 80[1] | 0.5 | 0.5 | 2.0 | 0.65 | 11.80 | | 1.35 | 0.5 | 11.80 |
| Simethicone[2] | 0.2 | 0.2 | 0.15 | 0.30 | 1.80 | | 0.21 | 0.2 | 1.80 |
| Listerine[3] | 83.35 | | | | | | | 83.35 | |
| Methylcellulose | 6.0 | | | | | | | | |
| Cornstarch[4] | | | 1.75 | | | | | | |
| Agar | | | 1.25 | | | | | | |
| Water | | 42.24 | 93.63 | 39.22 | 768.00 | 280.0 | 88.24 | | 768.0 |
| Loratadine[5] | | | | | 19.2 | | | | 19.2 |
| Pullulan[6] | | | | | | | | 6.0 | |
| Ibuprofen | | | | | | | | | 38.4 |

[1]Available from ICI Americas
[2]Available from OSI
[3]Available from Pfizer, Inc. including thymol (0.064%), eucalyptol (0.092%), methyl salicylate (0.060%), menthol (0.042%), water (up to 72.8%), alcohol (26.9%), benzoic acid, poloxamer 407, sodium benzoate, and caramel color
[4]Available from Grain Processing Corporation as Pure Cote B792
[5]Available from Schering Corporation as Claritin
[6]Available from Hayashibara Biochemical Laboratories, Inc., Japan The ingredients of inventive compositions A-I were combined by mixing until a uniform mixture as achieved. The compositions were then formed into a film by reverse roll coating. These films were then dried on the top side of an infrared transparent surface, the bottom side of which as in contact with a heated water bath at approximately 99° C. No external thermal air currents were present above the film. The films were dried to less than about 6% by weight water in about 4 to 6 minutes. The films were flexible, self-supporting and provided a uniform distribution of the components within the film.

The uniform distribution of the components within the film was apparent by examination by either the naked eye or under slight magnification. By viewing the films it was apparent that they were substantially free of aggregation, i.e. the carrier and the actives remained substantially in place and did not move substantially from one portion of the film to another. Therefore, there was substantially no disparity among the amount of active found in any portion of the film.

Uniformity was also measured by first cutting the film into individual dosage forms. Twenty-five dosage forms of substantially identical size were cut from the film of inventive composition (E) above from random locations throughout the film. Then eight of these dosage forms were randomly selected and additively weighed. The additive weights of eight randomly selected dosage forms, are as shown in Table 2 below:

TABLE 2

| | Additive Weight (g) | |
|---|---|---|
| Sample | Trial 1 | Trial 2 |
| 1 | 0.04 | 0.04 |
| 2 | 0.08 | 0.08 |
| 3 | 0.12 | 0.12 |
| 4 | 0.16 | 0.16 |
| 5 | 0.20 | 0.20 |
| 6 | 0.24 | 0.24 |
| 7 | 0.28 | 0.28 |

TABLE 2-continued

| | Additive Weight (g) | |
|---|---|---|
| Sample | Trial 1 | Trial 2 |
| 8 | 0.32 | 0.32 |

The individual dosages were consistently 0.04 gm, which shows that the distribution of the components within the film was consistent and uniform. This is based on the simple principal that each component has a unique density. Therefore, when the components of different densities are combined in a uniform manner in a film, as in the present invention, individual dosages forms from the same film of substantially equal dimensions, will contain the same mass.

An alternative method of determining the uniformity of the active is to cut the film into individual doses. The individual doses may then be dissolved and tested for the amount of active in films of particular size. This demonstrates that films of substantially similar size cut from different locations on the same film contain substantially the same amount of active.

When the films formed from inventive compositions A-H are placed on the tongue, they rapidly dissolve, releasing the active ingredient. Similarly, when they are placed in water, the films rapidly dissolve which provides a flavored drink when the active is chosen to be a flavoring.

Thin films that have a controlled degradation time and include combinations of water soluble and water insoluble polymers and water soluble films that allow controlled release of an active are prepared using approximately the amounts described in Table 3.

TABLE 3

| Ingredient | Weight (g) | | |
|---|---|---|---|
| | J | K | L |
| Hydroxypropylmethyl cellulose | | 1.0 | 1.0 |
| Tween 80[1] | 0.7 | 0.7 | 0.7 |
| Water | | | 5.0 |
| Aquacoat ECD[2] | 17.0 | 17.0 | 17.5 |
| Peppermint oil | 1.0 | 0.4 | 1.1 |

[1] Available from ICI Americas
[2] A 30% by weight aqueous dispersion of ethyl cellulose available from FMC The components of inventive compositions J-L were combined and formed into films using the methods for preparing inventive compositions A-I above. These films were also flexible, self-supporting and provided a uniform distribution of active which permits accuracy in dosing.

The uniformity of the films prepared from inventive compositions J-L may also be tested by either visual means measuring the weights of individual dosage films, or by dissolving the films and testing for the amount of active as described above.

An alternative method of preparing films which provides an accurate dosing may be used for any of inventive compositions A-I. The method begins with first combining the ingredients with mixing. The combination of ingredients is then divided among individual wells or molds. In such a method, aggregation of the components during drying is prevented by the individual wells.

TABLE 4

| Ingredient | Weight % | | |
|---|---|---|---|
| | M | N | O |
| 5% Methylcellulose Solution[1] | 73.22 | 44.22 | 74.22 |
| Raspberry Flavor | 3.28 | 3.28 | 3.28 |
| Sweetener Blends | 1.07 | 1.07 | 1.07 |
| Tween-80[2] | 2.47 | 2.47 | 2.47 |
| Polyvinylpyrrolidone | 3.30 | 3.30 | 3.30 |
| Ethanol 95% | 8.24 | 8.24 | 8.24 |
| Propylene Glycol | 1.65 | 1.65 | 1.65 |
| Calcium Carbonate | 4.12 | 4.12 | 4.12 |
| Cornstarch[3] | 1.65 | 1.65 | 1.65 |
| Red Dye[4] | 1.00 | | |
| Corn Syrup[5] | | | 30.00 |

[1] Available from Dow Chemical Co. as Methocel K35
[2] Available from ICI Americas
[3] Available from Grain Processing Corporationas Pure Cote B792
[4] Available from McCormick
[5] Available from Bestfoods, Inc. as Karo Syrup The ingredients in the above Table 4 were combined and formed into a film by casting the combination of ingredients onto the glass surface and applying heat to the bottom side of the glass. This provided inventive compositions M-O.

The film of composition M was examined both prior to and after drying for variations in the shading provided by the red dye. The film was examined both under sunlight and by incandescent bulb light. No variations in shade or intensity of color were observed.

Further testing of the films of composition M included testing of absorption which is directly related to concentration. The film was cut into segments each measuring 1.0 in. by 0.75 in., which were consecutively assigned numbers. Approximately 40 mg of the scrap material from which the segments were cut was dissolved in about 10 ml of distilled water and then quantitatively transferred to a 25 ml volumetric flask and brought to volume. The solution was centrifuged and scanned at 3 nm intervals from 203-1200 nm. The frequency of maximum absorption was found to be 530 nm. The solution was then re-centrifuged at a higher RPM (for the same length of time) and re-scanned, which demonstrated no change in the % transmission or frequency.

Each of the segments were weighed to 0.1 mg and then dissolved in 10 ml distilled water and transferred quantitatively to a 25 ml volumetric flask and brought to volume with distilled water. Each segment solution was then centrifuged as above, and then scanned, at first from 203-1200 nm and later from only 500 mn to 550 nm at a 1 nm scanning speed. The value recorded w2 as the % transmission at the lowest wave length, which was most frequently 530 nm.

The absorption values are shown in Table 5 below:

TABLE 5

| Segment | mg/% A |
|---|---|
| 1-2 | 1.717 |
| 3-4 | 1.700 |
| 5-6 | 1.774 |
| 7* | 1.701 |
| 9-10 | 1.721 |
| 11-12 | 1.729 |
| 13-14 | 1.725 |
| 15-16 | 1.713 |

*segment 8 was lost

The overall average absorption was 1.724. Of the 15 segments tested, the difference between the highest and lowest values was 0.073 units, or 4% based on the average. This shows excellent control over the uniformity of the dye within the composition because the absorption is directly proportional to the concentration of the dye within each segment.

The film of inventive composition N provided a very flexible film. This film was able to be stretched and exhibited a very high tensile strength.

After forming the film of inventive composition O, the film was removed from the glass by very rapidly stripping the length of the glass with a razor. This provided very tightly wound "toothpick-like" dosage forms. Each dosage form consistently weighed 0.02 g. This demonstrates the uniformity of the dosage forms as well as the superior self-supporting properties of the films.

TABLE 6

| Ingredient | Weight (g) | | | | | | | |
|---|---|---|---|---|---|---|---|---|
| | P | Q | R | S | T | U | V | W |
| Hydroxypropylmethyl cellulose | 320 | 320 | 320 | 320 | 320 | 320 | 345 | 345 |
| Water | 1440 | 1440 | 1440 | 1440 | | 1440 | 999 | 999 |
| Sweetener | | | | | | 60 | 60 | 45 |
| Mint Flavor | | | | | | 80 | 80 | |
| Propylene | 50 | 50 | 50 | 100 | 100 | 100 | 100 | 69.3 |

TABLE 6-continued

| | Weight (g) | | | | | | | |
|---|---|---|---|---|---|---|---|---|
| Ingredient | P | Q | R | S | T | U | V | W |
| Glycol | | | | | | | | |
| Xanthan | 22 | | 11 | 11.23 | 10 | 10 | 10 | 6.9 |
| Water/ Ethanol (60/40) | | | | | 1440 | | | |
| Orange Flavor | | | | | | | | 42 |

TABLE 7

| | Film Thickness (Micron) | *1 Top v (m/sec) | *1 Bottom v (m/sec) | *1 T (° C.) | *2 Top v (m/sec) | *2 Bottom v (m/sec) | *2 T (° C.) | Film Weight (g) | Coater Speed m/min | % Moisture |
|---|---|---|---|---|---|---|---|---|---|---|
| P1 | 100 | 0 | 22 | 75 | 0 | 23 | 60 | 109 | 5 | >20 |
| P2 | 350 | 0 | 22 | 75 | 0 | 23 | 60 | n/a | 5 | >20 |
| P3 | 350 | 0 | 40 | 75 | 0 | 40 | 60 | 161 | 3 | >20 |
| P4 | 350 | 0 | 40 | 75 | 0 | 40 | 75 | 191 | 3 | >20 |
| P5 | 350 | 10 | 40 | 75 | 10 | 40 | 75 | 253 | 3 | >20 |
| Q | 350 | 0 | 40 | 75 | 10 | 40 | 75 | n/a | 3 | >20 |
| R | 350 | 0 | 40 | 85 | 10 | 0 | 85 | | 2.5 | >20 |
| S1 | 250 | 0 | 40 | 100 | 0 | 40 | 90 | 163 | 1.5 | <5 |
| S2 | 300 | 0 | 40 | 100 | 0 | 40 | 90 | 193 | 1.5 | <5 |
| S3 | 350 | 0 | 40 | 100 | 0 | 40 | 90 | 225 | 1.5 | <5 |
| T1 | 250 | 0 | 40 | 100 | 0 | 40 | 90 | 64 | 1.5 | <5 |
| T2 | 350 | 0 | 40 | 100 | 0 | 40 | 90 | 83 | 1.5 | <5 |
| U1 | 300 | 0 | 40 | 100 | 0 | 40 | 90 | 208 | 1.5 | 20 |
| U2 | 250 | 0 | 40 | 100 | 0 | 40 | 90 | 177 | 1.5 | 20 |
| U3 | 300 | 0 | 40 | 100 | 0 | 40 | 90 | 212 | 1.3 | 20 |
| V1 | 300 | 0 | 40 | 100 | 0 | 40 | 90 | 237 | 1.3 | 20 |
| V2 | 300 | 0 | 40 | 100 | 0 | 40 | 100 | 242 | 1.3 | 20 |
| V3 | 300 | 0 | 40 | 100 | 0 | 40 | 100 | 221 | 1 | 6 |
| W1 | 300 | 0 | 40 | 93 | 0 | 40 | 90 | 220 | 1.3 | 5 |
| W2 | 250 | 0 | 40 | 90 | 0 | 40 | 90 | 199 | 1.3 | 5 |
| W3 | 200 | 0 | 40 | 90 | 0 | 40 | 90 | 169 | 1.3 | 5 |

*1 First Heater Section (3m)
*2 Second Heater Section (3m)

Compositions P-W were prepared to demonstrate the interaction among various conditions in production of films as they relate to the present invention. The ingredients in the above Table 6 were combined and formed into a film using the process parameters listed in Table 7 above, prepared in a 6 m drying tunnel designed to incorporate bottom drying of the films. Each of the examples shows the effect of different ingredient formulations and processing techniques on the resultant film products.

In Table 7, each of the process parameters contributes to different properties of the films. Film thickness refers to the distance between the blade and the roller in the reverse roll coating apparatus. Bottom velocity and top velocity refer to the speed of air current on the bottom and top sides of the film, respectively. The film weight is a measure of the weight of a circular section of the substrate and the film of 100 cm².

Compositions P-R show the effects of visco-elastic properties on the ability to coat the film composition mixture onto the substrate for film formation. Composition P displayed a stringy elastic property. The wet film would not stay level, the coating was uneven, and the film did not dry. In Composition Q, substantially the same formulation as P was used however the xanthan was not included. This product coated the substrate but would not stay level due to the change in the visco-elastic properties of the wet foam. Composition R was prepared using substantially the same formulation, but incorporated one-half of the amount of xanthan of Composition P. This formulation provided a composition that could be evenly coated. Compositions P-Q demonstrate the importance of proper formulation on the ability of the film matrix to conform to a particular coating technique.

The films produced from Composition S contained a large amount of air in the films. This is shown by the dried film thickness which was the same despite that variation in the coated thickness as in Table 7. Microscopic examination of the film revealed a large number of air bubbles in the film. In order to correct for the addition of air in the films, care must be taken in the mixing process to avoid air inclusion.

Composition T included a change in the solvent to 60/40 water ethanol. Composition T was stirred slowly for 45 min. to deaerate the mixture. The dried weight film products T1 and T2 was consistent with the increase in solids from T1 to T2. The films dried much faster with less than 5% moisture. With the particular combination of ingredients in Composition T, the substitution of part ethanol for part water allowed the film to dry more quickly. The elimination of air from the film as a result of the slow stirring also contributed to the uniformity of the final film product and the faster drying time.

Only water was used as a solvent in Composition U. The dried weight of the U1- U3 changed consistently in accordance with the change in coating thickness indicating that no air bubbles were present. However, these films contained 20% moisture upon exit from the oven, unlike the films of Composition T, which included partethanol and dried completely.

The amount of solids was increased and the amount of water was decreased in Compositions V1and V2. The dried weight was greater than U1-U3 due to the increase in solids, however the films still contained 20% moisture upon exit from the oven, similar to Composition U.

The coating line speed was reduced for Composition V3, to prevent premature drying of the exposed top film surface. This film product dried to 6% moisture.

While increasing the amount of solids improved the film weight, longer drying times were required. This was due to the surface of the film sealing preventing easy removal of the water. Therefore, For Compositions W1-W3, the temperature in the first 3m section of the dryer was decreased. This prevenled the premature drying of the top surface of the films. Even at greater ftlm thicknesses, the films were dried to 5% moisture even at faster coater line speeds.

TABLE 8

| Ingredient | Weight (g) | | | |
|---|---|---|---|---|
| | X | Y | Z | AA |
| Loratadine | 104.69 | | | |
| Zomig | | 52.35 | | |
| Paxil | | | 104.69 | |
| Hydroxypropyl methylcellulose | 320 | 320 | 320 | 150 |
| Sweetener blend | 60 | 60 | 60 | 0.4 |
| Dimethicone | 1.5 | 1.5 | 1.5 | 1.5 |
| Propylene glycol | 100 | 100 | 100 | |
| Water | 1440 | 1440 | 1440 | 790 |
| Cream essence | | | | 0.4 |
| Polyvinyl pyrrolidinone | | | | 4 |
| Ethanol | | | | 40 |
| Cocoa | | | | 55.2 |
| Polyoxyl-40-stearate | | | | 7 |

Compositions X, Y and Z of Table 8 were taste mask coated using a Glatt coater and Eudragit E-100 polymethacrylate polymer as the coating. The coating was spray coated at a 20% level. Therefore 10 mg of drug 12.5 mg of the final dry product must be weighed.

The base formula which excluded the drug additive was mixed with care to not incorporate air. After initial mixing the formula was slowly mixed to deaerate over 30 min. During this time the drug was weighed and prepared for addition to the base mix.

For Composition X, the Loratadine (80% drug) was added slowly to the mix with stirring. After 5 min. of stirring, the total mix was added to the pan of a three roll coater set (reverse roll coater) at 30 micron coating thickness.

The process bottom temperature was set at 90° C. with no top heat or air, the bottom air velocity was set at 40 m/sec., and the line speed was set at 1.3 m/min. Total drying time for the film was 4.6 min.

The liquid was coated at 30 microns and dried in the oven in less than 5 min. The film was flexible and a 1×0.75" piece weighed 70 mg and contained 10 mg of Loratadine.

The experiment was repeated for Compositions Y and Z, Zomig and Paxil, respectively. Both produced flexible films with the target weight of 70 mg containing 5 mg of Zomig and 70 mg containing 10 mg of Paxil, respectively.

The products were sweet without any noticeable drug aftertaste.

The ingredients of Composition AA were mixed in order to reduce air captured in the fluid matrix. After mixing 45 g of loratadine coated at a 80% active level and 20% coating using Eudragit E-100, this mixture was added slowing with mixing until the drug was evenly dispersed, approximately 5 min. The liquid was then deposited into the 3 roll coater (reverse roll coater) and coated at 30 microns at a line speed of 1.3 m/min. The oven temperature was set at 90° C. to apply air and heat to the bottom only, with an air velocity set at 40 m/sec. The dried film was 0.005 inch. thick (5 mil) and was cut into 1 in.×0.75 in. pieces weighing 70 mg±0.7 mg, demonstrating the uniformity of the composition of the film. The film was flexible with 5% moisture, free of air bubbles, and had uniform drug distribution as seen under the light microscope, as well as shown by the substantially identical weight measurements of the film pieces.

While there have been described what are presently believed to be the preferred embodiments of the invention, those skilled in the art will realize that changes and modifications may be made thereto without departing from the spirit of the invention, and it is intended to include all such changes and modifications as fall within the true scope of the invention.

What is claimed is:

1. A process for making a self supporting, edible film having a substantially uniform distribution of components comprising:
   (a) mixing an edible water-soluble polymer component, water and an active component comprising drug particles to form an edible matrix with a compositionally uniform distribution of said components;
   (b) deaerating said matrix by mixing;
   (c) forming a wet film from said deaerated matrix by coating or coating the film;
   (d) providing a surface having top and bottom sides;
   (e) feeding said film onto said top side of said surface; and
   (f) drying said film within about 10 minutes or fewer,
      wherein said drying step further comprises:
      (i) rapidiy forming a visco-elastic film having said drug particles uniformly distributed throughout within about the first 4.0 minutes by applying hot air currents at temperatures of about 60° C. to about 100° C. to said bottom side of said surface with substantially no top air flow to prevent flow migration and intermolecular forces from creating aggregates or conglomerates of said drug particles thereby maintaining the compositional uniform distribution of components; and
      (ii) further drying said visco-elastic film to form a self-supporting edible film having drug particles uniformly distributed throughout.

2. The process according to claim 1, wherein said active component is taste masked.

3. The process according to claim 1, wherein said wet film has a thickness of at least about 30 μm.

4. The process according to claim 1, wherein said wet film has a thickness of at least about 500 μm.

5. The process according to claim 1, wherein said wet film has a viscosity of about 400cps to about 100,000cps.

6. The process according to claim 1, further comprising the step of removing said self-supporting film from said surface.

7. The process according to claim 6, further comprising the step of dividing said self-supporting film into individual dosage forms of substantially equal dimensions.

8. The process according to claim 7, further comprising the step of packaging each of said individual dosage forms.

9. The process according to claim 1, wherein said self-supporting film is formed in conjunction with a removable backing.

10. A process for making a self-supporting, edible film dosage unit having a substantially uniform distribution of components comprising:
   (a) providing a wet matrix having a uniform distribution of edible components, said components comprising a water-soluble polymer component, an active component comprising drug particles and water to form an edible matrix with a compositionally uniform distribution of said components;
   (b) deaerating said matrix by mixing to prevent cavitation of the matrix in a manner which pulls air into the matrix;

(c) forming a wet film from said deaerated wet matrix by coating or casting the film;

(d) drying said film within about 10 minutes or fewer, wherein said drying step further comprises:

(i) rapidly forming a visco-elastic film having said drug particles uniformly distributed throughout within about the first 4.0 minutes by applying hot air currents at temperatures of about 60° C. to about 100° C. to said film to prevent flow migration and intermolecular forces from creating aggregates or conglomerates of said drug particles thereby maintaining the compositional uniform distribution of components; and (ii) further drying said visco-elastic film to form a self-supporting edible film having drug particles uniformly distributed throughout; and (e) dividing said self-supporting film into dosage forms of substantially equal dimensions, wherein each of said dosage forms is compositionally equal.

11. The process according to claim 10, wherein each of said dosage forms has substantially the same mass.

12. The process according to claim 10, wherein each of said dosage forms has substantially the same thickness.

13. A process for making a self-supporting, edible film having a substantially uniform distribution of components comprising:

(a) providing a wet matrix having a uniform distribution of edible components, said components comprising a water-soluble polymer component, an active component comprising drug particles and water to form an edible matrix with a compositionally uniform distribution of said components;

(b) deaerating said matrix by mixing to prevent cavitation of the matrix, thereby reducing formation of air bubbles;

(c) forming a wet film from said deaerated wet matrix by coating or casting the film, said film having a top surface, a bottom surface and a depth between said top and bottom surfaces; and (d) drying said film within about 10 minutes or fewer, wherein said drying step further comprises:

(i) rapidiy forming a visco-elastic film having said drug particles uniformly distributed throughout within about the first 4.0 minutes by applying hot air currents at temperatures of about 60° C. to about 100° C. to said film to prevent flow migration and intermolecular forces from creating aggregates or conglomerates of said drug particles thereby maintaining the compositional uniform distribution of components; and (ii) further drying said visco-elastic film to form a self-supporting edible film having drug particles uniformly distributed throughout, said dried film having a uniform distribution of said polymer and said solvent components, a uniform weight and a uniform thickness.

14. A process for making a self-supporting, edible film having a substantially uniform distribution of components comprising:

(a) providing a wet matrix having a uniform distribution of edible components, said components comprising a water-soluble polymer component, an active component comprising drug particles and water to form an edible matrix with a compositionally uniform distribution of said components;

(b) deaerating said matrix by mixing;

(c) forming a wet film from said deaerated wet matrix within a time period before the active degrades by coating or casting the film, said film having a top surface, a bottom surface and a depth between said top and bottom surfaces; and (d) drying said film within about 10 minutes or fewer, wherein said drying step further comprises:

(i) rapidiy forming a visco-elastic film having said drug particles uniformly distributed throughout within about the first 4.0 minutes by applying hot air currents at temperatures of about 60° C. to about 100° C. to said film to initiate drying of the depth of said film prior to forming a polymer skin on said top surface of said film and to prevent flow migration and intermolecular forces from creating aggregates or conglomerates of said drug particles thereby maintaining the compositional uniform distribution of components; and (ii) further drying said visco-elastic film to form a self-supporting edible film having drug particles uniformly distributed throughout, said dried film having a uniform distribution of said polymer and said solvent components, a uniform weight and a uniform thickness.

15. A process for making a self-supporting, edible film having a substantially uniform distribution of components comprising:

(a) providing a wet matrix having a uniform distribution of edible components, said components comprising a water-soluble polymer component, an active component comprising drug particles and water to form an edible matrix with a compositionally uniform distribution of said components;

(b) deaerating said matrix by mixing to reduce formation of air bubbles;

(c) forming a wet edible film from said deaerated wet matrix by coating or casting the film, said film having a top surface and a bottom surface; and (d) drying said film within about 10 minutes or fewer, wherein said drying step further comprises:

(i) rapidly forming a visco-elastic film having said drug particles uniformly distributed throughout within about the first 4.0 minutes by applying hot air currents at temperatures of about 60° C. to about 100° C. to said film, wherein said air currents are applied to said bottom surface of said film at a velocity greater than to said top surface of said film to prevent flow migration and intermolecular forces from creating aggregates or conglomerates of said drug particles thereby maintaining the compositional uniform distribution of components; and (ii) further drying said visco-elastic film to form a self-supporting edible film having drug particles uniformly distributed throughout.

16. The process according to claim 15, wherein said air currents applied to said top surface of said film are less than that which cause surface rippling or skinning prior to drying of the depth of said film.

17. A process for making a self-supporting, edible film having a substantially uniform distribution of components comprising:

(a) providing a wet matrix having a uniform distribution of edible components, said components comprising a water-soluble polymer component, a pharmaceutical active component comprising drug particles and water to form an edible matrix with a compositionally uniform distribution of said components;

(b) deaerating said matrix by mixing;

(c) forming a wet edible film from said deaerated wet matrix by coating or casting the film, said film having a top surface, a bottom surface and a depth of at least about 500µm between said top and bottom surfaces; and (d) drying said film within about 10 minutes or fewer, wherein said drying step further comprises:

(i) rapidly forming a visco-elastic film having said drug particles uniformly distributed throughout within about the first 4.0 minutes by applying hot air currents at temperatures of about 60° C. to about 100° C. to said film, wherein said air currents are less than that which cause surface rippling or skinning prior to drying of the depth of said film, to prevent flow migration and intermolecular forces from creating aggregates or conglomerates of said drug particles thereby maintaining the compositional uniform distribution of components; and (ii) further drying said visco-elastic film to form a self-supporting edible film having drug particles uniformly distributed throughout.

18. A process for making a self-supporting, edible film having a substantially uniform distribution of components comprising:

(a) providing a wet matrix having a uniform distribution of edible components, said components comprising a water-soluble polymer component, an active component comprising drug particles and water to form an edible matrix with a compositionally uniform distribution of said components;

(b) deaerating said matrix by mixing;

(c) forming a wet edible film from said deaerated wet matrix by coating or casting the film, said film having a top surface, a bottom surface and a depth between said top and bottom surfaces; and (d) drying said film within about 10 minutes or fewer, wherein said drying step further comprises:

(i) rapidly forming a visco-elastic film having said drug particles uniformly distributed throughout within about the first 4.0 minutes by applying hot air currents at temperatures of about 60° C. to about 100° C. to said film to prevent flow migration and intermolecular forces from creating aggregates or conglomerates of said drug particles thereby maintaining the compositional uniform distribution of components; and (ii) further drying said visco-elastic film, wherein said dried film is self-supporting and has drug particles uniformly distributed throughout and said top surface of said dried film is non-rippled.

19. A process for making a self-supporting, edible film having a substantially uniform. distribution of components comprising:

(a) combining and mixing an edible water-soluble polymer component, an active component comprising drug particles and water to form an edible matrix with a compositionally uniform distribution of said components;

(b) deaerating said matrix by mixing to reduce air bubble inclusions and applying a vacuum;

(c) forming an edible film from said deaerated matrix by coating or casting the film, said film having a top surface and a bottom surface; and (d) drying said film within about 10 minutes or fewer, wherein said drying step further comprises:

(i) drying said film from said bottom surface to said top surface by applying hot air currents at temperatures of about 60° C. to about 100° C. to said bottom surface of said film until a visco-elastic film having said drug particles uniformly distributed throughout is achieved within about the first 4.0 minutes; and (ii) further drying said visco-elastic film to form a self supporting edible film having drug particles uniformly distributed throughout.

20. A process for making a self supporting, edible film having a substantially uniform distribution of components comprising:

(a) providing a wet matrix having a uniform distribution of edible components, said components comprising a water-soluble polymer component, an active component comprising drug particles water and to form an edible matrix with a compositionally uniform distribution of components;

(b) deaerating said matrix by mixing;

(c) forming a wet edible film from said deaerated wet matrix by coating or casting the film, said film having a top surface, a bottom surface and a depth between said top and bottom surfaces; and (d) drying said film within about 10 minutes or fewer, wherein said drying step further comprises:

(i) rapidiy forming a visco-elastic film having said drug particles uniformly distributed throughout within about the first 4.0 minutes by applying hot air currents at temperatures of about 60° C. to about 100° C. to said film, wherein said air currents are insufficient to cause one or more of the following:

(i) surface skinning prior to drying the depth of said film;
(ii) surface rippling;
(iii) self aggregation of components;
(iv) non-uniformity in the thickness of said film; and
(v) non-uniformity of mass per unit volume; and (ii) further drying said visco-elastic film to form a self-supporting edible film having drug particles uniformly distributed throughout.

21. A process for making a self supporting, edible film having a substantially uniform distribution of components comprising:

(a) combining and mixing an edible water-soluble polymer component, an edible active component comprising drug particles and water to form an edible matrix with a compositionally uniform distribution of components;

(b) adding an anti-foaming agent to release oxygen from said mixture of components;

(c) further deaerating said matrix by mixing;

(d) forming a wet edible film from said deaerated matrix by coating or casting the film;

(e) providing a surface having top and bottom sides;

(f) feeding said wet film onto said top side of said surface; and (g) drying said film within about 10 minutes or fewer, wherein said drying step further comprises:

(i) rapidly forming a visco-elastic film having said drug particles uniformly distributed throughout within about the first 4.0 minutes by directing hot air currents at temperatures of about 60° C. to about 100° C. at said bottom side of said surface to prevent air flow migration and intermolecular forces from creating aggregates or conglomerates of said drug particles thereby maintaining the compositional uniform distribution of components; and (ii) further drying said visco-elastic film to form a self-supporting edible film having drug particles uniformly distributed throughout.

22. A process for making a self-supporting, edible film having a substantially uniform distribution of components comprising:

(a) forming a masterbatch premix of an edible water-soluble polymer component and water;

(b) deaerating said premix by mixing;

(c) feeding a predetermined amount of said deaerated premix via a first metering pump and a control valve to at least one of a first mixer and a second mixer;

(d) adding an active component comprising drug particles that degrade with prolonged exposure to water to at least one of said first and second mixers;
(e) mixing said active component and said predetermined amount of said premix to form a matrix having a uniform distribution of components;
(f) feeding an amount of said matrix to a pan through at least one second metering pump;
(g) forming a wet film from said matrix within a time period before the active degrades by coating or casting the film with one or more rollers;
(h) providing a surface having top and bottom sides;
(i) feeding said film onto said top side of said surface;
(j) drying said film within about 10 minutes or fewer, wherein said drying step further comprises:

(i) rapidly forming a visco-elastic film having said drug particles uniformly distributed throughout within about the first 4.0 minutes by applying hot air currents at temperatures of about 60° C. to about 100° C. to said bottom side of said surface with substantially no top air flow to prevent air flow migration and intermolecular forces from creating aggregates or conglomerates of said drug particles thereby maintaining the compositional uniform distribution of components; and
(ii) further drying said visco-elastic film to form a self supporting edible film having drug particles uniformly distributed throughout; and
(k) removing said self supporting film from said surface.

* * * * *

UNITED STATES PATENT AND TRADEMARK OFFICE
CERTIFICATE OF CORRECTION

PATENT NO. : 7,425,292 C1
APPLICATION NO. : 90/012097
DATED : July 3, 2012
INVENTOR(S) : Yang et al.

Page 1 of 1

It is certified that error appears in the above-identified patent and that said Letters Patent is hereby corrected as shown below:

Title Page, item (73);
Please correct the Assignee on the face of the Reexamination Certificate to recite: MonoSol Rx, LLC.

Signed and Sealed this
Second Day of October, 2012

David J. Kappos
*Director of the United States Patent and Trademark Office*

(12) EX PARTE REEXAMINATION CERTIFICATE (9115th)
United States Patent
Yang et al.

(10) Number: US 7,425,292 C1
(45) Certificate Issued: Jul. 3, 2012

(54) THIN FILM WITH NON-SELF-AGGREGATING UNIFORM HETEROGENEITY AND DRUG DELIVERY SYSTEMS MADE THEREFROM

(75) Inventors: Robert K. Yang, Flushing, NY (US); Richard C. Fuisz, McLean, VA (US); Gary L. Myers, Kingsport, TN (US); Joseph M. Fuisz, McLean, VA (US)

(73) Assignee: Philip Morris USA Inc., Richmond, VA (US)

Reexamination Request:
No. 90/012,097, Jan. 20, 2012

Reexamination Certificate for:
Patent No.: 7,425,292
Issued: Sep. 16, 2008
Appl. No.: 10/074,272
Filed: Feb. 14, 2002

Related U.S. Application Data

(60) Provisional application No. 60/328,868, filed on Oct. 12, 2001.

(51) Int. Cl.
*B32B 43/00* (2006.01)
*A61K 9/00* (2006.01)
*A61K 9/16* (2006.01)
*A61K 9/70* (2006.01)
*B29D 7/01* (2006.01)

(52) U.S. Cl. .................... 264/172.19; 264/212; 264/217
(58) Field of Classification Search .................. None
See application file for complete search history.

(56) References Cited

To view the complete listing of prior art documents cited during the proceeding for Reexamination Control Number 90/012,097, please refer to the USPTO's public Patent Application Information Retrieval (PAIR) system under the Display References tab.

*Primary Examiner* — Alan Diamond

(57) ABSTRACT

The invention relates to the film products and methods of their preparation that demonstrate a non-self-aggregating uniform heterogeneity. Desirably the films disintegrate in water and may be formed by a controlled drying process, or other process that maintains the required uniformity of the film.

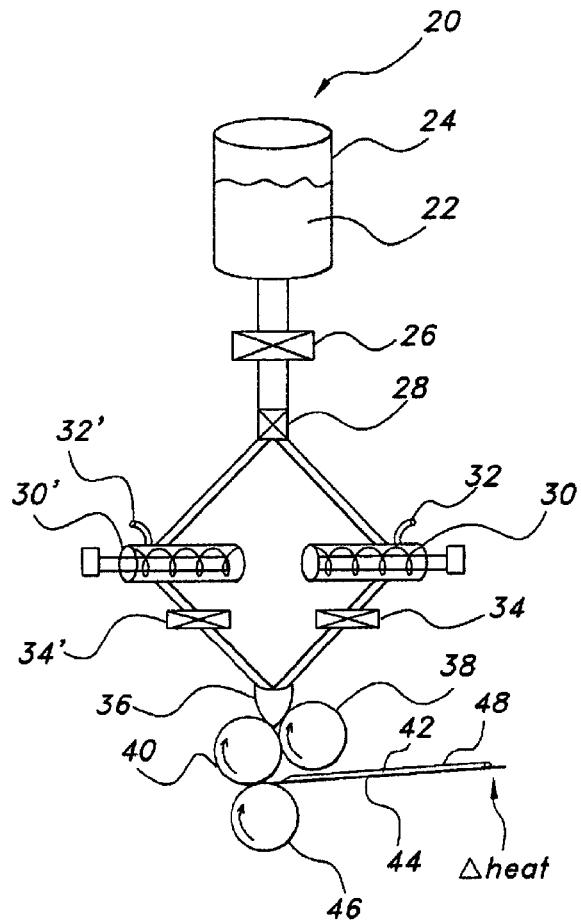

US 7,425,292 C1

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 10, 13-15 and 17-22 are determined to be patentable as amended.

Claims 2-9, 11, 12 and 16 dependent on an amended claim, are determined to be patentable.

New claims 23-55 are added and determined to be patentable.

1. A process for making a self supporting, edible film having a substantially uniform distribution of components comprising:
   (a) mixing an edible water-soluble polymer component, water and an active component comprising drug particles to form an edible matrix with a compositionally uniform distribution of said components *including said active component*; (b) deaerating said matrix by mixing; (c) forming a wet film from said deaerated matrix by coating or coating the film; (d) providing a surface having top and bottom sides; (e) feeding said film onto said top side of said surface; and (f) drying said film within about 10 minutes or fewer, wherein said drying step further comprises: (i) [rapidiy] *rapidly* forming a visco-elastic film having *active component comprising* drug particles uniformly distributed throughout *by rapidly increasing the viscosity of said film upon initiation of drying* within about the first 4.0 minutes by applying hot air currents at temperatures of about 60° C. to about 100° C. to said bottom side of said surface with substantially no top air flow to prevent flow migration and intermolecular forces from creating aggregates or conglomerates of said drug particles thereby maintaining the compositional uniform distribution of components *including said active component*; and (ii) further drying said visco-elastic film to form a self-supporting edible film having *active component comprising* drug particles uniformly distributed throughout, *whereby said compositional uniform distribution is measured by substantially equally sized individual unit doses which do not vary by more than 10% of active component.*

10. A process for making a self-supporting, edible film dosage unit having a substantially uniform distribution of components comprising:
   (a) providing a wet matrix having a uniform distribution of edible components, said components comprising a water-soluble polymer component, an active component comprising drug particles and water to form an edible matrix with a compositionally uniform distribution of said components *including said active component*; (b) deaerating said matrix by mixing to prevent cavitation of the matrix in a manner which pulls air into the matrix; (c) forming a wet film from said deaerated wet matrix by coating or casting the film; (d) drying said film within about 10 minutes or fewer, wherein said drying step further comprises: (i) rapidly forming a visco-elastic film having said *active component comprising* drug particles uniformly distributed throughout *by rapidly increasing the viscosity of said film upon initiation of drying* within about the first 4.0 minutes by applying hot air currents at temperatures of about 60° C. to about 100° C. to said film to prevent flow migration and intermolecular forces from creating aggregates or conglomerates of said drug particles thereby maintaining the compositional uniform distribution of components *including said active component*; and (ii) further drying said visco-elastic film to a self-supporting edible film having *active component comprising* drug particles uniformly distributed throughout; and (e) dividing said self-supporting film into dosage forms of substantially equal dimensions, wherein each of said dosage forms is compositionally equal, *whereby said compositional uniform distribution is measured by said substantially equally sized dosage forms which do not vary by more than 10% of active component.*

13. A process for making a self-supporting, edible film having a substantially uniform distribution of components comprising:
   (a) providing a wet matrix having a uniform distribution of edible components, said components comprising a water-soluble polymer component, an active component comprising drug particles and water to form an edible matrix with a compositionally uniform distribution of said components *including said active component*; (b) deaerating said matrix by mixing to prevent cavitation of the matrix, thereby reducing formation of air bubbles; (c) forming a wet film from said deaerated wet matrix by coating or casting the film, said film having a top surface, a bottom surface and a depth between said top and bottom surfaces; and (d) drying said film within about 10 minutes or fewer, wherein said drying step further comprises: (i) rapidly forming a visco-elastic film having said *active component comprising* drug particles uniformly distributed throughout *by rapidly increasing the viscosity of said film upon initiation of drying* within about the first 4.0 minutes by applying hot air currents at temperatures of about 60° C. to about 100° C. to said film to prevent flow migration and intermolecular forces from creating aggregates or conglomerates of said drug particles thereby maintaining the compositional uniform distribution of components *including said active component*; and (ii) further drying said visco-elastic film to form a self-supporting edible film having *active component comprising* drug particles uniformly distributed throughout, said dried film having a uniform distribution of said polymer and said solvent components, a uniform weight and a uniform thickness, *whereby said compositional uniform distribution is measured by substantially equally sized individual unit doses which do not vary by more than 10% of active component.*

14. A process for making a self-supporting, edible film having a substantially uniform distribution of components comprising:
   (a) providing a wet matrix having a uniform distribution of edible components, said components comprising a water-soluble polymer component, an active component comprising drug particles and water to form an edible matrix with a compositionally uniform distribution of said components *including said active component*; (b) deaerating said matrix by mixing; (c) forming a wet film from said deaerated wet matrix within a time period before the active degrades by coating or casting the film, said film having a top surface, a bottom surface and a depth between said top and bottom surfaces; and (d) drying said film within about 10 minutes or fewer, wherein said drying step further comprises: (i) rapidly forming a visco-elastic film having said *active component comprising* drug particles uniformly distributed throughout *by rapidly increasing the viscosity of said film upon initiation of drying* within about the first 4.0 minutes by applying hot air currents at temperatures of about 60° C. to about 100° C. to said film to initiate drying of the depth of said film prior to forming a polymer skin on said top surface of said film and to prevent flow migration and intermolecular forces from creating aggregates or conglomerates of said drug particles thereby maintaining the compositional uniform distribution of components *including said active component*; and (ii) further drying said visco-elastic film to form a self-supporting edible film having *active component comprising* drug particles uniformly distributed throughout, said dried film having a uniform distribution of said polymer and said solvent components, a uniform weight and a uniform thickness, *whereby said compositional uniform distribution is measured by substantially equally sized individual unit doses which do not vary by more than 10% of active component.*

15. A process for making a self-supporting, edible film having a substantially uniform distribution of components comprising:

(a) providing a wet matrix having a uniform distribution of edible components, said components comprising a water-soluble polymer component, an active component comprising drug particles and water to form an edible matrix with a compositionally uniform distribution of said components *including said active component*; (b) deaerating said matrix by mixing to reduce formation of air bubbles; (c) forming a wet edible film from said deaerated wet matrix by coating or casting the film, said film having a top surface and a bottom surface; and (d) drying said film within about 10 minutes or fewer, wherein said drying step further comprises: (i) rapidly forming a visco-elastic film having said *active component comprising* drug particles uniformly distributed throughout *by rapidly increasing the viscosity of said film upon initiation of drying* within about the first 4.0 minutes by applying hot air currents at temperatures of about 60° C. to about 100° C. to said film, wherein said air currents are applied to said bottom surface of said film at a velocity greater than to said top surface of said film to prevent flow migration and intermolecular forces from creating aggregates or conglomerates of said drug particles thereby maintaining the compositional uniform distribution of components *including said active component*; and (ii) further drying said visco-elastic film to form a self-supporting edible film having *said active component comprising* drug particles uniformly distributed throughout, *whereby said compositional uniform distribution is measured by substantially equally sized individual unit doses which do not vary by more than 10% of active component.*

17. A process for making a self-supporting, edible film having a substantially uniform distribution of components comprising:

(a) providing a wet matrix having a uniform distribution of edible components, said components comprising a water-soluble polymer component, a pharmaceutical active component comprising drug particles and water to form an edible matrix with a compositionally uniform distribution of said components *including said active component*; (b) deaerating said matrix by mixing; (c) forming a wet edible film from said deaerated wet matrix by coating or casting the film, said film having a top surface, a bottom surface and depth of at least about 500 μm between said top and bottom surfaces; and (d) drying said film within about 10 minutes or fewer, wherein said drying step further comprises: (i) rapidly forming a visco-elastic film having said *active component comprising* drug particles uniformly distributed throughout *by rapidly increasing the viscosity of said film upon initiation of drying* within about the first 4.0 minutes by applying hot air currents at temperatures of about 60° C. to about 100° C. to said film, wherein said air currents are less than that which cause surface rippling or skinning prior to drying of the depth of said film, to prevent flow migration and intermolecular forces from creating aggregates or conglomerates of said drug particles thereby maintaining the compositional uniform distribution of components *including said active component*; and (ii) further drying said visco-elastic film to form a self-supporting edible film having *active component comprising* drug particles uniformly distributed throughout, *whereby said compositional uniform distribution is measured by substantially equally sized individual unit doses which do not vary by more than 10% of active component.*

18. A process for making a self-supporting, edible film having a substantially uniform distribution of components comprising:

(a) providing a wet matrix having a uniform distribution of edible components, said components comprising a water-soluble polymer component, an active component comprising drug particles and water to form an edible matrix with a compositionally uniform distribution of said components *including said active component*; (b) deaerating said matrix by mixing: (c) forming a wet edible film from said deaerated wet matrix by coating or casting the film, said film having a top surface, a bottom surface and a depth between said top and bottom surfaces; and (d) drying said film within about 10 minutes or fewer, wherein said drying step further comprises: (i) rapidly forming a visco-elastic film having said *active component comprising* drug particles uniformly distributed throughout *by rapidly increasing the viscosity of said film upon initiation of drying* within about the first 4.0 minutes by applying hot air currents at temperatures of about 60° C. to about 100° C. to said film to prevent flow migration and intermolecular forces from creating aggregates or conglomerates of said drug particles thereby maintaining the compositional uniform distribution of components *including said active component*; and (ii) further drying said visco-elastic film, wherein said dried film is self-supporting and has *active component comprising* drug particles uniformly distributed throughout and said top surface of said dried film is non-rippled, *whereby said compositional uniform distribution is measured by substantially equally sized individual unit doses which do not vary by more than 10% of active component.*

19. A process for making a self-supporting, edible film having a substantially uniform distribution of components comprising:

(a) combining and mixing an edible water-soluble polymer component, an active component comprising drug particles and water to form an edible matrix with a compositionally uniform distribution of said components *including said active component*; (b) deaerating said matrix by mixing to reduce air bubble inclusions and applying a vacuum; (c) forming an edible film from said deaerated matrix by coating or casting the film, said film having a top surface and a bottom surface; and (d) drying said film within about 10 minutes or fewer, wherein said drying step further comprises: (i) drying said film from said bottom surface to said top surface *by rapidly increasing the viscosity of said film upon initiation of drying* by applying hot air currents at temperatures of about 60° C. to about 100° C. to said bottom surface of said film unitl a visco-elastic film having said *active component comprising* drug particles uniformly distributed throughout is achieved within about the first 4.0 minutes; and (ii) further drying said visco-elastic film to form a self supporting edible film having *active component comprising* drug particles uniformly distributed throughout, *whereby said compositional uniform distribution is measured by substantially equally sized individual unit doses which do not vary by more than 10% of active component.*

20. A process for making a self supporting, edible film having a substantially uniform distribution of components comprising:

(a) providing a wet matrix having a uniform distribution of edible components, said components comprising a water-soluble polymer component, an active component comprising drug particles water and to form an edible matrix with a compositionally uniform distribution of components *including said active component*; (b) deaerating said matrix by mixing; (c) forming a wet edible film from said deaerated wet matrix by coating or casting the film, said film having a top surface, a bottom surface and a depth between said top and bottom surfaces; and (d) drying said film within about 10 minutes or fewer, wherein said drying step further comprises: (i) rapidly forming a visco-elastic film having said *active component comprising* drug particles uniformly distributed throughout *by rapidly increasing the viscosity of said film upon initiation of drying* within about the first 4.0 minutes by applying hot air currents at temperatures of about 60° C. to about 100° C. to said film, wherein said air currents are insufficient to cause one or more of the following: (i) surface skinning prior to drying the depth of said film; (ii) surface rippling; (iii) self aggregation of components; (iv) non-uniformity in the thickness of said film; and (v) non-uniformity of mass per unit volume; and (ii) further drying said visco-elastic film to form a self-supporting edible film having *said active component comprising* drug particles uniformly distributed throughout, *whereby said compositional uniform distribution is measured by substantially equally sized individual unit doses which do not vary by more than 10% of active component.*

21. A process for making a self supporting, edible film having a substantially uniform distribution of components comprising:

(a) combining and mixing an edible water-soluble polymer component, an edible active component comprising drug particles and water to form an edible matrix with a compositionally uniform distribution of components *including said active component*; (b) adding an anti-foaming agent to release oxygen from said mixture of components; (c) further deaerating said matrix by mixing; (d) forming a wet edible film from said deaerated matrix by coating or casting the film; (e) providing a surface having top and bottom sides; (f) feeding said wet film onto said top side of said surface; and (g) drying said film within about 10 minutes or fewer, wherein said drying step further comprises: (i) rapidly forming a visco-elastic film having said *active component comprising* drug particles uniformly distributed throughout *by rapidly increasing the viscosity of said film upon initiation of drying* within about the first 4.0 minutes by directing hot air currents at temperatures of about 60° C. to about 100° C. at said bottom side of said surface to prevent air flow migration and intermolecular forces from creating aggregates or conglomerates of said drug particles thereby maintaining the compositional uniform distribution of components *including said active component*; and (ii) further drying said visco-elastic film to form a self-supporting edible film having *active component comprising* drug particles uniformly distributed throughout, *whereby said compositional uniform distribution is measured by substantially equally sized individual unit doses which do not vary by more than 10% of active component.*

22. A process for making a self-supporting, edible film having a substantially uniform distribution of components comprising:

(a) forming a masterbatch premix of an edible water-soluble polymer component and water; (b) deaerating said premix by mixing; (c) feeding a predetermined amount of said deaerated premix via a first metering pump and a control valve to at least one of a first mixer and a second mixer; (d) adding an active component comprising drug particles that degrade with prolonged exposure to water to at least one of said first and second mixers; (e) mixing said active component and said predetermined amount of said premix to form a matrix having a uniform distribution of components *including said active component*; (f) feeding an amount of said matrix to a pan through at least one second metering pump; (g) forming a wet film from said matrix within a time period before the active degrades by coating or casting the film with one or more rollers; (h) providing a surface having top and bottom sides; (i) feeding said film onto said top side of said surface; (j) drying said film within about 10 minutes or fewer, wherein said drying step further comprises: (i) rapidly forming a visco-elastic film having said *active component comprising* drug particles uniformly distributed throughout *by rapidly increasing the viscosity of said film upon initiation of drying* within about the first 4.0 minutes by applying hot air currents at temperatures of about 60° C. to about 100° C. to said bottom side of said surface with substantially no top air flow to prevent air flow migration and intermolecular forces from creating aggregates or conglomerates of said drug particles thereby maintaining the compositional uniform distribution of components *including said active component*; and (ii) further drying said visco-elastic film to form a self supporting edible film having *active component comprising* drug particles uniformly distributed throughout; and (k) removing said self supporting film from said surface, *whereby said compositional uniform distribution is measured by substantially equally sized individual unit doses which do not vary by more than 10% of active component.*

23. The process of claim 1, wherein said step of further drying said visco-elastic film comprises drying to obtain a self-supporting edible film having a water content of no more than 10% by weight.

24. The process of claim 10, wherein said step of further drying said visco-elastic film comprises drying to obtain a self-supporting edible film having a water content of no more than 10% by weight.

25. The process of claim 13, wherein said step of further drying said visco-elastic film comprises drying to obtain a self-supporting edible film having a water content of no more than 10% by weight.

26. The process of claim 14, wherein said step of further drying said visco-elastic film comprises drying to obtain a self-supporting edible film having a water content of no more than 10% by weight.

27. The process of claim 15, wherein said step of further drying said visco-elastic film comprises drying to obtain a self-supporting edible film having a water content of no more than 10% by weight.

28. The process of claim 17, wherein said step of further drying said visco-elastic film comprises drying to obtain a self-supporting edible film having a water content of no more than 10% by weight.

29. The process of claim 18, wherein said step of further drying said visco-elastic film comprises drying to obtain a self-supporting edible film having a water content of no more than 10% by weight.

30. The process of claim 19, wherein said step of further drying said visco-elastic film comprises drying to obtain a self-supporting edible film having a water content of no more than 10% by weight.

31. The process of claim 20, wherein said step of further drying said visco-elastic film comprises drying to obtain a self-supporting edible film having a water content of no more than 10% by weight.

32. The process of claim 21, wherein said step of further drying said visco-elastic film comprises drying to obtain a self-supporting edible film having a water content of no more than 10% by weight.

33. The process of claim 22, wherein said step of further drying said visco-elastic film comprises drying to obtain a self-supporting edible film having a water content of no more than 10% by weight.

34. The process of claim 1, wherein said step of feeding said wet film onto the top surface comprises feeding said wet film onto the top surface of an already-formed film layer.

35. The process of claim 10, wherein said step of coating or casting said wet film comprises coating or casting said wet film onto the top surface of an already-formed film layer.

36. The process of claim 13, wherein said step of coating or casting said wet film comprises coating or casting said wet film onto the top surface of an already-formed film layer.

37. The process of claim 14, wherein said step of coating or casting said wet film comprises coating or casting said wet film onto the top surface of an already-formed film layer.

38. The process of claim 15, wherein said step of coating or casting said wet film comprises coating or casting said wet film onto the top surface of an already-formed film layer.

39. The process of claim 17, wherein said step of coating or casting said wet film comprises coating or casting said wet film onto the top surface of an already-formed film layer.

40. The process of claim 18, wherein said step of coating or casting said wet film comprises coating or casting said wet film onto the top surface of an already-formed film layer.

41. The process of claim 19, wherein said step of coating or casting said edible film comprises coating or casting said edible film onto the top surface of an already-formed film layer.

42. The process of claim 20, wherein said step of coating or casting said wet film comprises coating or casting said wet film onto the top surface of an already-formed film layer.

43. The process of claim 21, wherein said step of feeding said wet film onto the top surface comprises feeding said wet film onto the top surface of an already-formed film layer.

44. The process of claim 22, wherein said step (i) of feeding said film comprises feeding said film onto the top surface of an already-formed film layer.

45. The process of claim 1, wherein said active component is in the form of a solution, emulsion, or suspension.

46. The process of claim 10, wherein said active component is in the form of a solution, emulsion, or suspension.

47. The process of claim 13, wherein said active component is in the form of a solution, emulsion, or suspension.

48. The process of claim 14, wherein said active component is in the form of a solution, emulsion, or suspension.

49. The process of claim 15, wherein said active component is in the form of a solution, emulsion, or suspension.

50. The process of claim 17, wherein said active component is in the form of a solution, emulsion, or suspension.

51. The process of claim 18, wherein said active component is in the form of a solution, emulsion, or suspension.

52. The process of claim 19, wherein said active component is in the form of a solution, emulsion, or suspension.

53. The process of claim 20, wherein said active component is in the form of a solution, emulsion, or suspension.

54. The process of claim 21, wherein said active component is in the form of a solution, emulsion, or suspension.

55. The process of claim 22, wherein said active component is in the form of a solution, emulsion, or suspension.

\* \* \* \* \*